(12) United States Patent
Adams et al.

(10) Patent No.: US 7,301,021 B2
(45) Date of Patent: Nov. 27, 2007

(54) SUBSTITUTED IMIDAZOLE COMPOUNDS

(75) Inventors: Jerry L. Adams, Wayne, PA (US); Ralph F. Hall, Villanova, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 1111 days.

(21) Appl. No.: 10/147,530

(22) Filed: May 17, 2002

(65) Prior Publication Data
US 2003/0114452 A1  Jun. 19, 2003

Related U.S. Application Data

(62) Division of application No. 09/446,147, filed as application No. PCT/US98/13809 on Jul. 1, 1998, now Pat. No. 6,489,325.

(60) Provisional application No. 60/051,592, filed on Jul. 2, 1997.

(51) Int. Cl.
C07D 213/02 (2006.01)
C07D 215/00 (2006.01)
C07D 253/06 (2006.01)
A61K 31/44 (2006.01)
A61K 31/47 (2006.01)

(52) U.S. Cl. .................. 544/123; 544/315; 514/235.8; 514/274

(58) Field of Classification Search ................ 544/123, 544/315; 514/235.8, 274
See application file for complete search history.

(56) References Cited

U.S. PATENT DOCUMENTS

| | | | |
|---|---|---|---|
| 2,833,779 A | 5/1958 | Fields | |
| 3,707,475 A | 12/1972 | Lombardino | 260/309 |
| 3,772,441 A | 11/1973 | Lombardino | 424/273 |
| 3,929,807 A | 12/1975 | Fitzi | 260/294.8 R |
| 3,940,486 A | 2/1976 | Fitzi | 424/263 |
| 4,058,614 A | 11/1977 | Baldwin | 424/263 |
| 4,199,592 A | 4/1980 | Cherkofsky | 424/273 |
| 4,447,431 A | 5/1984 | Sallmann | 424/246 |
| 4,503,065 A | 3/1985 | Wilkerson | 514/396 |
| 4,565,875 A | 1/1986 | Cavender | 548/336 |
| 4,686,231 A | 8/1987 | Bender et al. | 514/333 |
| 4,822,805 A | 4/1989 | Takasugi et al. | 514/341 |
| 5,593,992 A | 1/1997 | Adams et al. | 514/235.8 |
| 5,756,499 A | 5/1998 | Adams et al. | 514/235.8 |
| 5,777,097 A | 7/1998 | Lee et al. | 536/24.31 |
| 5,783,664 A | 7/1998 | Lee et al. | 530/350 |
| 5,864,036 A | 1/1999 | Adams et al. | 544/123 |
| 5,869,043 A | 2/1999 | McDonnell et al. | 424/94.1 |
| 5,916,891 A | 6/1999 | Adams et al. | 514/256 |
| 5,977,103 A | 11/1999 | Adams et al. | 514/235.2 |
| 6,361,773 B1 | 3/2002 | Lee et al. | 424/139.1 |

FOREIGN PATENT DOCUMENTS

| | | |
|---|---|---|
| EP | 0 477 049 | 3/1992 |
| WO | WO91/19497 | 12/1991 |
| WO | WO92/10190 | 6/1992 |
| WO | WO92/10498 | 6/1992 |
| WO | WO93/14081 | 7/1993 |

(Continued)

OTHER PUBLICATIONS

Armarego, W. J. Chem. Soc., (JCSOA9) p. 561 (1962).

(Continued)

*Primary Examiner*—James O. Wilson
*Assistant Examiner*—Paul V. Ward
(74) *Attorney, Agent, or Firm*—Dara L. Dinner; Stephen Venetianer; Charles M. Kinzig

(57) ABSTRACT

Novel 1,4,5-substituted imidazole compounds and compositions for use in therapy as CSBP/p38 kinase inhibitors.

51 Claims, 2 Drawing Sheets

FOREIGN PATENT DOCUMENTS

| | | |
|---|---|---|
| WO | WO93/14082 | 7/1993 |
| WO | WO95/02591 | 1/1995 |
| WO | WO95/03297 | 2/1995 |
| WO | WO95/13067 | 5/1995 |
| WO | WO95/31451 | 11/1995 |
| WO | WO96/21452 | 7/1996 |
| WO | WO96/21654 | 7/1996 |
| WO | WO96/40143 | 12/1996 |
| WO | WO97/05877 | 2/1997 |
| WO | WO97/05878 | 2/1997 |
| WO | WO97/12876 | 4/1997 |
| WO | WO97/16426 | 5/1997 |
| WO | WO97/16441 | 5/1997 |
| WO | WO97/16442 | 5/1997 |
| WO | WO97/25045 | 7/1997 |
| WO | WO97/25046 | 7/1997 |
| WO | WO97/25047 | 7/1997 |
| WO | WO97/25048 | 7/1997 |
| WO | WO97/23479 | 9/1997 |
| WO | WO97/32583 | 9/1997 |
| WO | WO97/33883 | 9/1997 |
| WO | WO97/35855 | 10/1997 |
| WO | WO97/35856 | 10/1997 |
| WO | WO97/36587 | 10/1997 |
| WO | WO97/47618 | 12/1997 |
| WO | WO98/07425 | 4/1998 |
| WO | WO98/16230 | 4/1998 |
| WO | WO98/22109 | 5/1998 |
| WO | WO98/47892 | 10/1998 |
| WO | WO98/52937 | 11/1998 |
| WO | WO98/52940 | 11/1998 |
| WO | WO98/52941 | 11/1998 |
| WO | WO98/56377 | 12/1998 |
| WO | WO98/56788 | 12/1998 |
| WO | WO98/57966 | 12/1998 |
| WO | WO99/01131 | 1/1999 |
| WO | WO99/01136 | 1/1999 |
| WO | WO99/01449 | 1/1999 |
| WO | WO99/01452 | 1/1999 |
| WO | WO99/03837 | 1/1999 |
| WO | WO99/17776 | 4/1999 |
| WO | WO99/18942 | 4/1999 |
| WO | WO99/32110 | 7/1999 |
| WO | WO99/32121 | 7/1999 |
| WO | WO99/42592 | 8/1999 |
| WO | WO99/57101 | 11/1999 |
| WO | WO99/57253 | 11/1999 |
| WO | WO99/58128 | 11/1999 |
| WO | WO99/58523 | 11/1999 |
| WO | WO99/61437 | 12/1999 |
| WO | WO99/61440 | 12/1999 |
| WO | WO 00/01688 | 1/2000 |
| WO | WO 00/06563 | 2/2000 |
| WO | WO 00/10563 | 3/2000 |
| WO | WO 00/17175 | 4/2000 |
| WO | WO 00/19824 | 4/2000 |
| WO | WO 00/23072 | 4/2000 |
| WO | WO 00/26209 | 5/2000 |
| WO | WO 00/31063 | 6/2000 |
| WO | WO 00/31065 | 6/2000 |
| WO | WO 00/39116 | 7/2000 |
| WO | WO 00/43384 | 7/2000 |
| WO | WO 00/59541 | 12/2000 |
| WO | WO 00/75131 | 12/2000 |
| WO | WO 01/19322 | 3/2001 |

OTHER PUBLICATIONS

Becker et al., J. Immunol., 147, p. 4307 (1991).
Boehm et al., J. Med. Chem. 39, pp. 3929-3937 (1996).
Bradlerova et al., Chem. Zvesti, 29 (6), pp. 795-802 (1975).
Colotta et al., J. Immunol., 132(2), p. 936 (1984).
de Silva et al., J. Chem. Soc., 4, pp. 685-690, (1995).
Dinarello et al., Rev.Infect.Disease, 6, p. 51 (1984).
Dinarello, J.Clin.Immun., 5(5), p. 287-297 (1985).
Engel & Steglich, Liebigs Ann. Chem., 1916 (1978).
Ferles et al., Collect. Czech. Chem. Commun., 5 (46), pp. 1167-1172 (1981).
Fischer et al., Rec.Trav.Chim.Pays.Bas., 84, p. 439 (1965).
Fulmer et al., J. Heterocycl. Chem., 17 (4), pp. 799-800 (1980).
Gallahger et al., Bioorganic & Medicinal Chem. vol. 5, No. 1, pp. 49-64 (1997).
Garigipati, R., Tetrahedron Letters, 31, p. 190 (1989).
Gilbert, Synthesis, pp. 30-32 (1972).
Ishibashi, Chem. Pharm. Bull., 37(8), pp. 2214-2216 (1989).
Johnson, P.A., J.Chem.Soc., Perkin Trans., vol. 1, pp. 895-905 (1996).
Jurkowski-Kowalczyk, Rocz. Chem., 51 (6), pp. 1191-1199 (1977).
Katritzky, Synthesis, pp. 45-47 (1993).
Kawasaki et al., J. Bio. Chem., 272(30), pp. 18518-18521.
Kumada et al., Tetrahedron Letters, 22, p. 5319 (1981).
Lamartina et al., Boll. Chim. Farm., 129 (12), pp. 314-316 (1990).
Mikailu et al., Zh. Obshch. Khim., 56 (7), pp. 1513-1517 (1986).
Morton et al., Tetrahedron Letters, 4123 (1982).
Poli et al., Proc.Nat'l Acad.Sci., 87, p. 782-784 (1990).
Pridgen, J.Org.Chem., 47, p. 4319 (1982).
R.P.Soni, Aust.J.Chem., 35, p. 1493-6 (1982).
Simon et al., J. Immunol. Methods, 84, p. 85 (1985).
Snieckus, V., Tetrahedron Letters, 29, 2135 (1988).
Stille, J.Amer.Chem.Soc., 109, p. 5478 (1978).
Strzybny et al., J. Org. Chem., 28, p. 3381 (1963).
Szucs et al., Chem. Zvesti, 26 (4), pp. 354-359 (1972).
Szucs et al., Acta fac. Pharm. Univ. Commenianae, 30, pp. 127-146 (1977).
Terashimia, M., Chem.Pharm.Bull., 11, p. 4755 (1985).
Thompson, W.J., et al., J.Org.Chem., 49, p. 5237 (1984).
Uno, Bull. Chem. Soc. Japan., vol. 69, pp. 1763-1767 (1996).
VanLeusen et al., J.O.C., 42, p. 1153 (1977).
Vartanyan et al., 40, (9), pp. 552-560 (1987).
Wilson et al., Chemistry & Biology, vol. 4, No. 6, pp. 423-431 (1997).
Zavyalov et al., Khim Farm Zh, 26(3), p. 88 (1992) (With Translation).

SUBSTITUTED IMIDAZOLE COMPOUNDS

This is a divisional application Ser. No. 09/446,147 filed 30 Mar. 2000 now U.S. Pat. No. 6,489,325 which is a §371 of International Application PCT/US98/13809, filed 1 Jul. 1998, which claims benefit from Provisional Application U.S. Ser. No. 60/051,592 filed 2 Jul. 1997.

FIELD OF THE INVENTION

This invention relates to a novel group of imidazole compounds, processes for the preparation thereof, the use thereof in treating CSBP/p38 mediated diseases and pharmaceutical compositions for use in such therapy.

BACKGROUND OF THE INVENTION

Intracellular signal transduction is the means by which cells respond to extracellular stimuli. Regardless of the nature of the cell surface receptor (e.g. protein tyrosine kinase or seven-transmembrane G-protein coupled), protein kinases and phosphatases along with phopholipases are the essential machinery by which the signal is further transmitted within the cell [Marshall, J. C. *Cell*, 80, 179–278 (1995)]. Protein kinases can be categorized into five classes with the two major classes being, tyrosine kinases and serine/threonine kinases depending upon whether the enzyme phosphorylates its substrate(s) on specific tyrosine(s) or serine/threonine(s) residues [Hunter, T., *Methods in Enzymology* (*Protein Kinase Classification*) p. 3, Hunter, T.; Sefton, B. M.; eds. vol. 200, Academic Press; San Diego, 1991].

For most biological responses, multiple intracellular kinases are involved and an individual kinase can be involved in more than one signaling event. These kinases are often cytosolic and can translocate to the nucleus or the ribosomes where they can affect transcriptional and translational events, respectively. The involvement of kinases in transcriptional control is presently much better understood than their effect on translation as illustrated by the studies on growth factor induced signal transduction involving MAP/ERK kinase [Marshall, C. J. *Cell*, 80, 179 (1995); Herskowitz, I. *Cell*, 80, 187 (1995); Hunter, T. *Cell*, 80, 225 (1995): Seger, R., and Krebs, E. G. *FASEB J.*, 726–735 (1995)].

While many signaling pathways are part of cell homeostasis, numerous cytokines (e.g., IL-1 and TNF) and certain other mediators of inflammation (e.g., COX-2, and iNOS) are produced only as a response to stress signals such as bacterial lippopolysaccharide (LPS). The first indications suggesting that the signal transduction pathway leading to LPS-induced cytokine biosynthesis involved protein kinases came from studies of Weinstein [Weinstein, et al., *J. Immunol.* 151, 3829(1993)] but the specific protein kinases involved were not identified. Working from a similar perspective, Han [Han, et al., *Science* 265, 808(1994)] identified murine p38 as a kinase which is tyrosine phosphorylated in response to LPS. Definitive proof of the involvement of the p38 kinase in LPS-stimulated signal transduction pathway leading to the initiation of proinflammatory cytokine biosynthesis was provided by the independent discovery of p38 kinase by Lee [Lee; et al., *Nature*, 372, 739(1994)] as the molecular target for a novel class of anti-inflammatory agents. The discovery of p38 (termed by Lee as CSBP 1 and 2) provided a mechanism of action of a class of anti-inflammatory compounds for which SK&F 86002 was the prototypic example. These compounds inhibited IL-1 and TNF synthesis in human monocytes at concentrations in, the low mM range [Lee, et al., *Int. J. Immunopharmac.* 10(7), 835(1988)] and exhibited activity in animal models which are refractory to cyclooxygenase inhibitors [Lee; et al., *Annals N.Y. Acad. Sci.*, 696, 149(1993)].

It is now firmly established that CSBP/p38 is a one of several kinases involved in a stress-response signal transduction pathway which is parallel to and largely independent of the analogous mitogen-activated protein kinase (MAP) kinase cascade (FIG. 1). Stress signals, including LPS, pro-inflammatory cytokines, oxidants, UV light and osmotic stress, activate kinases upstream from CSBP/p38 which in turn phosphorylate CSBP/p38 at threonine 180 and tyrosine 182 resulting in CSBP/p38 activation. MAPKAP kinase-2 and MAPKAP kinase-3 have been identified as downstream substrates of CSBP/p38 which in turn phosphorylate heat shock protein Hsp 27 (FIG. 2). It is not yet known whether MAPKAP-2, MAPKAP-3, Mnk1 or Mnk2 are involved in cytokine biosynthesis or alternatively that inhibitors of CSBP/p38 kinase might regulate cytokine biosynthesis by blocking a yet unidentified substrate downstream from CSBP/p38 [Cohen, P. *Trends Cell Biol.*, 353–361(1997)].

What is known, however, is that in addition to inhibiting IL-1 and TNF, CSBP/p38 kinase inhibitors (SK&F 86002 and SB 203580) also decrease the synthesis of a wide variety of pro-inflammatory proteins including, IL-6, IL-8, GM-CSF and COX-2. Inhibitors of CSBP/p38 kinase have also been shown to suppress the TNF-induced expression of VCAM-1 on endothelial cells, the TNF-induced phosphorylation and activation of cytosolic PLA2 and the IL-1-stimulated synthesis of collagenase and stromelysin. These and additional data demonstrate that CSBP/p38 is involved not only cytokine synthesis, but also in cytokine signaling [CSBP/P38 kinase reviewed in Cohen, P. *Trends Cell Biol.*, 353–361(1997)].

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic β cells [review of the biological activities which have been attributed to IL-1 Dinarello, *J. Clinical Immunology*, 5 (5), 287–297 (1985)].

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

Interleukin-8 (IL-8) is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutrophil into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

Inhibition of signal transduction via CSBP/p38, which in addition to IL-1, TNF and IL-8 described above is also required for the synthesis and/or action of several additional pro-inflammatory proteins (i.e., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for CSBP/p38 kinase inhibitors [Badger, et al., *J. Pharm. Exp. Thera* 279 (3): 1453–1461. (1996); Griswold, et al, *Pharmacol. Comm.* 7, 323–229 (1996)].

There remains a need for treatment, in this field, for compounds which are cytokine suppressive anti-inflammatory drugs, i.e. compounds which are capable of inhibiting the CSBP/p38/RK kinase.

SUMMARY OF THE INVENTION

Figure 1:
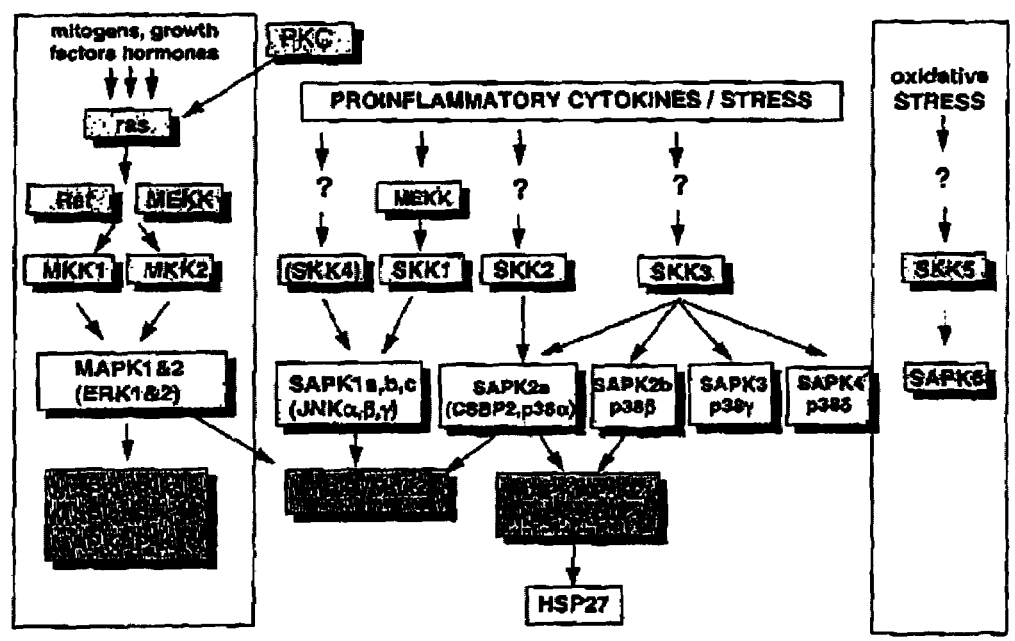
FIG. 1 demonstrates the Mitogen and Stress Activated Protein Kinase Cascades
Figure 2:
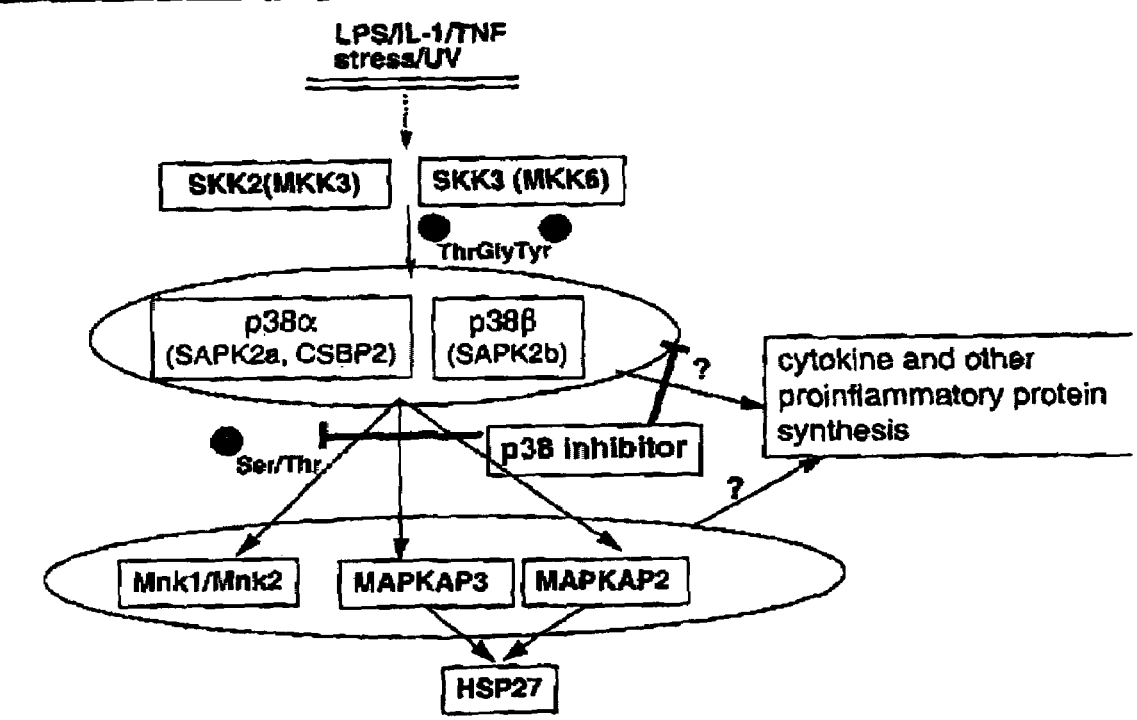
FIG. 2 demonstrates the p38 Kinase Pathway

This invention relates to the novel compounds of Formula (I) and pharmaceutical compositions comprising a compound of Formula (I) and a pharmaceutically acceptable diluent or carrier.

This invention relates to a method of treating a CSBP/RK/p38 kinase mediated disease in a mammal in need thereof, which comprises administering to said mammal an effective amount of a compound of Formula (I).

This invention also relates to a method of inhibiting cytokines and the treatment of a cytokine mediated disease, in a mammal in need thereof, which comprises administering to said mammal an effective amount of a compound of Formula (I).

This invention more specifically relates to a method of inhibiting the production of IL-1 in a mammal in need thereof which comprises administering to said mammal an effective amount of a compound of Formula (I).

This invention more specifically relates to a method of inhibiting the production of IL-8 in a mammal in need thereof which comprises administering to said mammal an effective amount of a compound of Formula (I).

This invention more specifically relates to a method of inhibiting the production of TNF in a mammal in need thereof which comprises administering to said mammal an effective amount of a compound of Formula (I).

Accordingly, the present invention provides a compound of Formula (I):

wherein $R_1$ is 4-pyridyl, pyrimidinyl, 4-pyridazinyl, 1,2,4-triazin-5-yl quinolyl, isoquinolinyl, or quinazolin-4-yl ring, which ring is substituted with $Y-R_a$ and optionally with an additional independent substituent selected from $C_{1-4}$ alkyl, halogen hydroxyl, $C_{1-4}$ alkoxy, $C_{1-4}$ alkylthio, $C_{1-4}$ alkylsulfinyl, $CH_2OR_{12}$, amino, mono and di-$C_{1-6}$ alkyl substituted amino, an N-heterocyclyl ring which ring has from 5 to 7 members and optionally contains an additional heteroatom selected from oxygen, sulfur or $NR_{15}$, $N(R_{10})C(O)R_b$ or $NHR_a$;

Y is oxygen or sulfur;

$R_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, $C(Z)NR_7R_{17}$, $C(Z)OR_{16}$, $(CR_{10}R_{20})_vCOR_{12}$, $SR_5$, $SOR_5$, $OR_{12}$, halo-substituted-$C_{1-4}$ alkyl, $C_{1-4}$ alkyl, $ZC(Z)R_{12}$, $NR_{10}C(Z)R_{16}$, or $(CR_{10}R_{20})_vNR_{10}R_{20}$ and which, for other positions of substitution, is halogen, cyano, $C(Z)NR_{13}R_{14}$, $C(Z)OR_3$, $(CR_{10}R_{20})_{m''}COR_3$, $S(O)_mR_3$, $OR_3$, halo-substituted-$C_{1-4}$ alkyl, $C_{1-4}$ alkyl, $(CR_{10}R_{20})_{m''}NR_{10}C(Z)R_3$, $NR_{10}S(O)_{m'}R_8$, $NR_{10}S(O)_{m'}NR_7R_{17}$, $ZC(Z)R_3$ or $(CR_{10}R_{20})_{m''}NR_{13}R_{14}$;

Z is oxygen or sulfur;

n is an integer having a value of 1 to 10;

m is 0, or the integer 1 or 2;

m' is an integer having a value of 1 or 2, m" is 0, or an integer having a value of 1 to 5;

v is 0, or an integer having a value of 1 or 2;

$R_2$ is $-C(H)(A)(R_{22})$;

A is an optionally substituted aryl, heterocyclyl, or heteroaryl ring, or A is a substituted $C_{1-10}$ alkyl;

$R_{22}$ is an optionally substituted $C_{1-10}$ alkyl;

$R_a$ is aryl, aryl $C_{1-6}$alkyl, heterocyclic, heterocyclyl$C_{1-6}$ alkyl, heteroaryl, or heteroaryl $C_{1-6}$alkyl, wherein each of these moieties may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl; and wherein each of these moieties may be optionally substituted;

$R_3$ is heterocyclyl, heterocyclyl$C_{1-10}$ alkyl or $R_8$;

$R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being SOH;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$; and wherein the aryl, arylalkyl, heteroaryl, heteroaryl alkyl may be optionally substituted;

$R_9$ is hydrogen, $C(Z)R_{11}$ or optionally substituted $C_{1-10}$ alkyl, $S(O)_2R_{18}$, optionally substituted aryl or optionally substituted aryl-$C_{1-4}$ alkyl;

$R_{10}$ and $R_{20}$ are each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl, wherein these moieites may be optionally substituted;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

$R_{15}$ is $R_{10}$ or $C(Z)$—$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$_{1-10}$ alkyl, heterocyclyl, heterocyclyl-$C_{1-10}$alkyl, heteroaryl or heteroaryl$_{1-10}$alkyl;

or a pharmaceutically acceptable salt thereof.

DETAILED DESCRIPTION OF THE INVENTION

In Formula (I), suitable $R_1$ moieties includes, 4-pyridyl, 4-pyrimidinyl, 4-pyridazinyl, 1,2,4-triazin-5-yl, 4-quinolyl, 6-isoquinolinyl, or 4-quinazolinyl rings, of which the 4-pyridyl, 4-pyrimidinyl and 4-quinolyl rings are preferred. More preferred is the 4-pyrimidinyl or 4-pyridyl moiety, and most preferred is the 4-pyrimidinyl ring.

The $R_1$ moiety is substituted with the Y—$R_a$ group wherein Y is oxygen or sulfur, and $R_a$ is aryl, aryl$C_{1-6}$alkyl, heterocyclic, heterocyclic$C_{1-6}$ alkyl, heteroaryl, or heteroaryl$C_{1-6}$alkyl; and wherein each of the $R_a$ moieties may be optionally substituted as defined below.

When $R_a$ is aryl, it is preferably phenyl or napthyl. When $R_a$ is arylalkyl, it it is preferably benzyl or napthylmethyl. When $R_a$ is a heterocyclic or heterocyclic alkyl moiety, the heterocyclic portion is preferably pyrrolindinyl, piperidinyl, morpholino, tetrahydropyranyl, tetrahydrothiopyranyl, tetrahydrothipyransulfinyl, tetrahydrothio-pyransulfonyl, pyrrolindinyl, indole, or piperonyl ring. It is noted that the heterocyclic rings herein may contain unsaturation, such as in a tryptamine ring.

When $R_a$ is a heteroaryl ring as defined below, it is preferably a pyridine or tetrazole ring.

The $R_a$ aryl, heterocyclic and heteroaryl rings may be optionally substituted one or more times, preferably one to three times, independently with halogen; $C_{1-4}$ alkyl, such as methyl, ethyl, propyl, isopropyl, or t-butyl; halosubstituted alkyl, such as $CF_3$; hydroxy; hydroxy substituted $C_{1-4}$ alkyl; $(CR_{10}R_{20})_q$ $C_{1-4}$ alkoxy, such as methoxy or ethoxy; $(CR_{10}R_{20})_qS(O)_m$alkyl and; $(CR_{10}R_{20})_qS(O)_m$ aryl (wherein m is 0, 1, or 2); $(CR_{10}R_{20})_qC(O)OR_{11}$, such as C(O) $C_{1-4}$ alkyl or C(O)OH moieties; $(CR_{10}R_{20})_qC(O)R_{11}$; $(CR_{10}R_{20})_q$OC(O)$R_c$; O—(CH$_2$)s-O; $(CR_{10}R_{20})_qNR_{13}R_{14}$; $(CR_{10}R_{20})_q$N($R_{10}$)C(O)$R_b$; $(CR_{10}R_{20})_qC(O)NR_{13}R_{14}$; $(CR_{10}R_{20})_qC(O)NR_{10}R_c$; $(CR_{10}R_{20})_qS(O)_2NR_{13}R_{14}$; $(CR_{10}R_{20})_qS(O)_2NR_{10}R_c$; $(CR_{10}R_{20})_qN(R_{10})S(O)_2R_c$; cyano, nitro, an N-heterocyclyl ring which ring has from, 5 to 7 members and optionally contains an additional heteroatom selected from oxygen, sulfur or $NR_{15}$; aryl, such as phenyl; an optionally substituted arylalkyl, such as benzyl or phenethyl; aryloxy, such as phenoxy; or arylalkyloxy such as benzyloxy; and wherein the aryl, alkylalkyl, aryloxy and arylalkyloxy containing moieties may be optionally substituted themselves one to two times by halogen, hydroxy, hydroxy substituted alkyl, $C_{1-10}$alkoxy, $S(O)_m$ alkyl, amino, $NR_7R_{17}$ group, $C_{1-14}$ alkyl, or halosubstituted $C_{1-4}$ alkyl.

Suitably, s is an integer having a value of 1, 2, or 3. Preferably s is 2 yielding a 1,3-dioxyethylene moiety, or ketal functionality.

Suitably, q is 0 or an integer having a value of 1 to 4.

Suitably, $R_b$ is hydrogen, $C_{1-6}$ alkyl, $C_{3-7}$ cycloalkyl, aryl, aryl $C_{1-4}$ alkyl, heteroaryl, heteroaryl $C_{1-4}$alkyl, heterocyclyl, or heterocyclyl $C_{1-4}$ alkyl moiety; all of which moieties may be optionally substituted as defined below.

Suitably, $R_c$ is an $C_{1-6}$ alkyl, $C_{3-7}$ cycloalkyl, aryl, aryl $C_{1-4}$ alkyl, heteroaryl, heteroaryl $C_{1-4}$alkyl, heterocyclyl, or heterocyclyl $C_{1-4}$ alkyl moiety; all of which moieties may be optionally substituted as defined below.

Suitable $R_a$ groups include, but are not limited to, benzyl, halosubstituted benzyl, napthylmethyl, phenyl, halosubstituted phenyl, aminocarbonylphenyl, alkylphenyl, cyanophenyl, alkylthiophenyl, hydroxyphenyl, alkoxyphenyl, phenoxyphenyl, benzyloxyphenyl, phenylphenyl, methylenedioxyphenyl, trifluoromethylphenyl, methylsulfonylphenyl, tetrazole, methyltetrazolyl, morpholinopropyl, piperonyl, piperidin-4-yl, alkyl substituted piperidine, such as 1-methyl piperidine, or 2,2,6,6-tetramethylpiperidin-4-yl.

Preferred ring substitution on the benzyl or phenyl rings is in the 4-position. Preferred substitution on the phenyl or phenyl alkyl groups is halogen, halosubstituted alkyl or alkyl groups, such as fluoro or chloro, or methyl.

It is recognized that the $R_1$ group may additionally be substituted one or more times independently by $C_{1-4}$ alkyl, halo, OH, $C_{1-4}$ alkoxy, $C_{1-4}$ alkylthio, $C_{1-4}$ alkylsulfinyl, $CH_2OR_{12}$, amino, mono- and di-$C_{1-6}$ alkyl substituted amino, $N(R_{10})C(O)R_b$, $NHR_a$ or an N-heterocyclyl ring which ring has from 5 to 7 members and optionally contains an additional heteroatom selected from oxygen, sulfur or $NR_{15}$.

When the additional $R_1$ optional substituent is $N(R_{10})C(O)R_b$, $R_b$ is preferably $C_{1-6}$ alkyl; preferably $R_{10}$ is hydrogen. It is also recognized that the $R_b$ moieties, in particular the $C_{1-6}$ alkyl group may be optionally substituted, preferably from one to three times, preferably with halogen, such as fluorine, as in trifluoromethyl or, trifluroethyl.

The preferred ring placement for $YR_a$ moiety on the 4-pyridyl derivative is in the 2-position, and a preferred ring placement on the 4-pyrimidinyl ring is also at the 2-position.

Suitably, $R_4$ is phenyl, naphth-1-yl or naphth-2-yl, or a heteroaryl, which is optionally substituted by one or two substituents. More preferably $R_4$ is a phenyl or naphthyl ring. Suitable substitutions for $R_4$ when this is a 4-phenyl, 4-naphth-1-yl, 5-naphth-2-yl or 6-naphth-2-yl moiety are one or two substituents each of which are independently selected from halogen, $SR_5$, $SOR_5$, $OR_{12}$, $CF_3$, or $(CR_{10}R_{20})_v$ $NR_{10}R_{20}$, and for other positions of substitution on these rings preferred substitution is halogen, $S(O)_mR_3$, $OR_3$, $CF_3$, $(CR_{10}R_{20})_{m''}NR_{13}R_{14}$, $NR_{10}C(Z)R_3$ and $NR_{10}S(O)_mR_8$.

When $R_4$ is a heteroaryl ring, the ring is substituted in a similar ring substitution pattern as for the phenyl ring, i.e. halogen, $SR_5$, $SOR_5$, $OR_{12}$, $CF_3$, or $(CR_{10}R_{20})_vNR_{10}R_{20}$.

Preferred substituents for the 4-position in phenyl and naphth-1-yl and on the 5-position in naphth-2-yl include halogen, especially fluoro and chloro and $SR_5$ and $SOR_5$ wherein $R_5$ is preferably a $C_{1-2}$ alkyl, more preferably methyl, of which the fluoro and chloro is more preferred, and most especially preferred is fluoro.

Preferred substituents for the 3-position in phenyl and naphth-1-yl rings include: halogen, especially fluoro and chloro; $OR_3$, especially $C_{1-4}$ alkoxy; $CF_3$, $NR_{10}R_{20}$, such as amino; $NR_{10}C(Z)R_3$, especially $NHCO(C_{1-10}$ alkyl); $NR_{10}S(O)_mR_8$, especially $NHSO_2(C_{1-10}$alkyl), and $SR_3$ and $SOR_3$ wherein $R_3$ is preferably a $C_{1-2}$ alkyl, more preferably methyl. When the phenyl ring is disubstituted preferably it is two independent halogen moieties, such as fluoro and chloro, preferably di-chloro and more preferably in the 3,4-position. It is also preferred that for the 3-position of both the $OR_3$ and $ZC(Z)R_3$ moietites, $R_3$ may also include hydrogen.

Preferably, the $R_4$ moiety is an unsubstituted or substituted phenyl moiety. More preferably, $R_4$ is phenyl or phenyl substituted at the 4-position with fluoro and/or substituted at the 3-position with fluoro, chloro, $C_{1-4}$ alkoxy, methanesulfonamido or acetamido, or $R_4$ is a phenyl di-substituted at the 3,4-position independently with chloro or fluoro, more preferably chloro. Most preferably, $R_4$ is a 4-fluorophenyl.

Suitably, Z is oxygen or sulfur, preferably oxygen.

Suitably, $R_3$ is heterocyclyl, heterocyclyl$C_{1-10}$ alkyl or $R_8$.

Suitably, $R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being SOH.

Suitably, $R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$C_{1-4}$alkyl, heterocyclyl, aroyl, or $C_{1-10}$ alkanoyl.

Suitably, $R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$.

Suitably, $R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl $C_{1-10}$ alkyl, heteroaryl, heteroaryl $C_{1-10}$ alkyl, $(CR_{10}R_{20})_nOR_{11}$, $(CR_{10}R_{20})_nS(O)_mR_{18}$, $(CR_{10}R_{20})_n$NHS $(O)_2R_{18}$, $(CR_{10}R_{20})_nNR_{13}R_{14}$; wherein the aryl, arylalkyl, heteroaryl, and heteroarylalkyl containing moieites may be optionally substituted.

Suitably, $R_9$ is hydrogen, $C(Z)R_{11}$ or optionally substituted $C_{1-10}$ alkyl, $S(O)_2R_{18}$, optionally substituted aryl or an optionally substituted aryl-$C_{1-4}$ alkyl.

Suitably, $R_{10}$ and $R_{20}$ are each independently selected from hydrogen or $C_{1-4}$ alkyl.

Suitably, $R_{11}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl; and wherein all of these moieties may be optionally substituted.

Suitably, $R_{12}$ is hydrogen or $R_{16}$; and $R_{16}$ is suitably, $C_{1-4}$ alkyl, halo-substituted-$C_{1-4}$ alkyl, or $C_{3-7}$ cycloalkyl.

Suitably, $R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$.

Suitably, $R_{15}$ is $R_{10}$ or $C(Z)$—$C_{1-4}$ alkyl.

Suitably, $R_{18}$ is $C_{1-10}$ alkyl, $C_{3-7}$ cycloalkyl, heterocyclyl, aryl, aryl$_{1-10}$alkyl, heterocyclyl, heterocyclyl-$C_{1-10}$alkyl, heteroaryl or heteroaryl$_{1-10}$alkyl.

Suitably, v is 0, or an integer having a value of 1 or 2.

Suitably, m is 0, or the integer 1 or 2.

Suitably, m' is an integer having a value of 1 or 2.

Suitably, m" is 0, or an integer having a value of 1 to 5.

Suitably, n is an integer having a value of 1 to 10.

$R_2$ is a substituted alkyl derivative. It is recognized that the first methylene carbon in this chain is a tertiary carbon, and it will contain one hydrogen moiety. This methylene group will have has two additional substituents, an $R_{22}$ moiety and an A moiety, i.e., $C(H)(A)(R_{22})$. Both A and $R_{22}$ may not be unsubstituted $C_{1-10}$ alkyl moieties.

In a preferred embodiment, $R_2$ is a $C(AA_1)(A)$ moiety, wherein $AA_1$ is the $R_{22}$ moiety, but is specifically the side chain residue (R) of an amino acid, as is further described herein.

Suitably, A is an optionally substituted $C_{3-7}$cycloalkyl, aryl, heteroaryl, or heterocyclic ring, or A is a substituted $C_{1-10}$ alkyl moiety.

When A is an aryl, heteroaryl and heterocyclic ring, the ring may be substituted independently one or more times, preferably, 1 to 3 times by $C_{1-10}$ alkyl; halogen; halo substituted $C_{1-10}$ alkyl, such as $CF_3$; $(CR_{10}R_{20})_tOR_{11}$; $(CR_{10}R_{20})_tNR_{13}R_{14}$, especially amino or mono- or di-$C_{1-4}$ alkylamino; $(CR_{10}R_{20})_tS(O)_mR_{18}$, wherein m is 0, 1 or 2; SH; $NR_{10}C(Z)R_3$ (such $NHCO(C_{1-10}$ alkyl)); or $NR_{10}S(O)_mR_8$ (such as $NHSO_2(C_{1-10}$ alkyl)).

Suitably, t is 0, or an integer of 1 to 4.

When A is an optionally substituted cycloalkyl it is as defined below in the $R_{22}$ substitution.

When A is an optionally substituted heterocyclyl ring, the ring is preferably a morpholino, pyrrolidinyl, piperazinyl or a piperidinyl ring.

When A is an optionally substituted aryl moiety, it is preferably a phenyl ring.

When A is an optionally substituted heteroaryl ring, the heteroaryl term is as defined below in the definition section.

When A is a substituted $C_{1-10}$ alkyl moiety, the alkyl chain may be straight or branched. The chain is substituted independently 1 or more times, preferably 1 to 3 times by halogen, such as fluorine, chlorine, bromine or iodine; halosubstituted $C_{1-10}$ alkyl, such as $CF_3$, $C_{3-7}$cycloalkyl, $C_{1-10}$ alkoxy, such as methoxy or ethoxy; hydroxy substituted $C_{1-10}$ alkoxy; halosubstituted $C_{1-10}$ alkoxy, such as $OCF_2CF_2H$; $OR_{11}$; $S(O)_mR_{18}$ (wherein m is 0, 1 or 2); $NR_{13}R_{14}$; $C(Z)NR_{13}R_{14}$; $S(O)_mNR_{13}R_{14}$; $NR_{23}C(Z)R_{11}$;

NHS(O)$_2$R$_{18}$; C(Z)R$_{11}$; OC(Z)R$_{11}$; C(Z)OR$_{11}$; C(Z)NR$_{11}$OR$_9$; N(OR$_6$)C(Z)NR$_{13}$R$_{14}$; N(OR$_6$)C(Z)R$_{11}$; C(=NOR$_6$)R$_{11}$; NR$_{23}$C(=NR$_{19}$)NR$_{13}$R$_{14}$; OC(Z)NR$_{13}$R$_{14}$; NR$_{23}$C(Z)NR$_{13}$R$_{14}$; or NR$_{23}$C(Z)OR$_{10}$.

Preferably, A is a C$_{3-7}$ cycloalkyl, or a C$_{1-6}$ alkyl, more preferably a C$_{1-2}$ alkyl, i.e. a methylene or ethylene moiety, more preferably a methylene moiety which is substituted by one of the above noted groups.

Preferably, when A is an alkyl derivative, it is substituted by OR$_{11}$ where R$_{11}$ is preferably hydrogen, aryl or arylalkyl; NR$_{13}$R$_{14}$; OC(Z)R$_{11}$; or C(Z)OR$_{11}$.

More preferably, A is substituted by OR$_{11}$ where R$_{11}$ is hydrogen.

Suitably, R$_{22}$ is a C$_{1-10}$ alkyl chain, which chain may be straight or branched and which may be optionally substituted independently, one or more times, preferably 1 to 3 times, by halogen, such as fluorine, chlorine, bromine or iodine; halo substituted C$_{1-10}$ alkyl; C$_{1-10}$ alkoxy, such as methoxy or ethoxy; hydroxy substituted C$_{1-10}$ alkoxy; halo-substituted C$_{1-10}$ alkoxy, such as OCF$_2$CF$_2$H; OR$_{11}$; S(O)$_m$R$_{18}$; NR$_{13}$R$_{14}$; C(Z)NR$_{13}$R$_{14}$; S(O)$_m$NR$_{13}$R$_{14}$; NR$_{23}$C(Z)R$_{11}$; NHS(O)$_2$R$_{18}$; C(Z)R$_{11}$; OC(Z)R$_{11}$; C(Z)OR$_{11}$; C(Z)NR$_{11}$OR$_9$; N(OR$_6$)C(Z)NR$_{13}$R$_{14}$; N(OR$_6$)C(Z)R$_{11}$; C(=NOR$_6$)R$_{11}$; NR$_{23}$C(=NR$_{19}$)NR$_{13}$R$_{14}$; OC(Z)NR$_{13}$R$_{14}$; NR$_{23}$q(Z)NR$_{13}$R$_{14}$; NR$_{23}$C(Z)OR$_{10}$; optionally substituted C$_{3-7}$ cycloalkyl; optionally substituted aryl, such as phenyl; optionally substituted heteroaryl; or an optionally substituted heterocyclic moiety. The optional substitutents on these cycloalkyl, aryl, heteroaryl, and heterocyclic moieties are as defined herein below.

It is noted that those R$_{22}$ substituent groups which contain carbon as the first connecting group, i.e. C(Z)OR$_{11}$; C(Z)NR$_{11}$OR$_9$, C(Z)R$_{11}$, C(Z)NR$_{13}$R$_{14}$, C(=NOR$_6$)R$_{11}$, may be the sole carbon in alkyl chain. Therefore, R$_{22}$ may, for instance, be a carboxy, an aldehyde, an amide, as well as being a substituent off a methylene unit, such as carbamoylmethyl, or acetamidomethyl. In other words, R$_{22}$ can be an optionally substituted alkyl group as defined above, or R$_{22}$ can be C(Z)OR$_{11}$, C(Z)NR$_{11}$R$_9$, C(Z)R$_{11}$, C(Z)NR$_{13}$R$_{14}$, or C(=NOR$_6$)R$_{11}$.

Preferably R$_{22}$ is a C$_{1-6}$ unsubstituted or substituted alkyl group, such as a C$_{1-3}$ alkylene, such as methyl, ethyl or isopropyl, or a methylene or ethylene moiety substituted by one of the above noted moieties, or as noted above those substituent groups which contain a carbon may substitutent for the first methylene unit of the alkyl chain, such as carboxy, C(O)OR$_{11}$, C(O)NR$_{13}$R$_{14}$, or R$_{22}$ is an optionally substitued aryl group, such as a benzyl or phenethyl.

Preferably R$_{22}$ is a C$_{1-6}$ unsubstituted or substituted alkyl group, more preferably a C$_{1-2}$ alkylene chain, such as a methylene or ethylene moiety, more preferably methylene.

Preferably the R$_{22}$ alkyl chain is substituted by OR$_{11}$, where R$_{11}$ is preferably hydrogen, aryl or arylalkyl; S(O)$_m$R$_{18}$, where m is 0 and R$_{18}$ is a C$_{1-6}$ alkyl; or an optionally substituted aryl, i.e. a benzyl or phenethyl moiety.

More preferably, R$_{22}$ is methyl, phenyl, benzyl, CH$_2$OH, or CH$_2$—O-aryl.

Preferably, one or both of A and R$_{22}$ contain hydroxy moieties, such as in C$_{1-6}$ alkyl OR$_{11}$, wherein R$_{11}$ is hydrogen, i.e. CH$_2$CH$_2$OH.

Suitably, when AA$_1$ is the (R) side chain residue of an amino acid, it is a C$_{1-6}$ alkyl group, which may be straight or branched. This means the R group off the core amino acid of the structure R—C(H) (COOH) (NH$_2$). The R residue term is for example, CH$_3$ for alanine, (CH$_3$)$_2$CH— for valine, (CH$_3$)$_2$CH—CH$_2$— for leucine, phenyl-CH$_2$— for phenylalanine, CH$_3$—S—CH$_2$—CH$_2$— for methionine, etc.

All generally recognized primary amino acids are included in this groups, such as but not limited to, alanine, arginine, asparagine, aspartic acid, cysteine, glutamine, glutamic acid, glycine, histidine, isoleucine, leucine, lysine, methionine, phenylalanine, serine, threonine, tryptophan, tyrosine, valine, hydroxylysine, methylhistidine, and other naturally occurring amino acids not found in proteins, such as b-alanine, g-aminobutyric acid, homocysteine, homoserine, citrulline, ornithine, canavanine, djenkolic acid, and b-cyanoalanine, or other naturally occurring non-mammalian amino acids.

Preferably AA$_1$ is the residue of phenylalanine, or alanine.

When R$_{22}$ is an optionally substituted heterocyclic moiety, the ring is preferably a morpholino, pyrrolidinyl, piperazinyl, or a piperidinyl group. When the heterocyclic ring is optionally substituted the substituents may be directly attached to the free nitrogen, such as in the piperidinyl group or pyrrole ring, or on the ring itself. Preferably the ring is a piperidine or pyrrole, more preferably piperidine.

The R$_{22}$ heterocyclyl ring may be optionally substituted one to four times independently by halogen; C$_{1-4}$ alkyl; aryl, such as phenyl; arylalkyl, such as benzyl, (and wherein the aryl or aryl alkyl moieties themselves may be optionally substituted as defined in the definition section below); C(O)OR$_{11}$, such as the C(O) C$_{1-4}$ alkyl or C(O)OH moieties; C(O)H; C(O) C$_{1-4}$ alkyl; hydroxy substituted C$_{1-4}$ alkyl; C$_{1-4}$ alkoxy; S(O)$_m$C$_{1-4}$ alkyl (wherein m is 0, 1, or 2); or NR$_{10}$R$_{20}$ (wherein R$_{10}$ and R$_{20}$ are independently hydrogen or C$_{1-4}$alkyl).

Preferably if the ring is a piperidine; the substituents are attached directly on the available nitrogen, i.e. a 1-Formyl-4-piperidine, 1-benzyl-4-piperidine, 1-methyl-4-piperidine, 1-ethoxycarbonyl-4-piperidine. If the ring is substituted by an alkyl group and the ring is attached in the 4-position, it is preferably substituted in the 2- or 6-position or both, such as 2,2,6,6-tetramethyl-4-piperidine. Similarly, if the ring is a pyrole, the substituents are all directly on the available nitrogen.

When the R$_{22}$ optional substituent is an optionally substituted aryl; it is preferably a phenyl; or when R$_{22}$ is an optionally substituted heteroaryl ring (as defined in the definition section below), the rings may be optionally substituted independently one or more times, preferably by one to three times by C$_{1-10}$ alkyl; halogen, especially fluoro or chloro; (CR$_{10}$R$_{20}$)$_t$OR$_{11}$; (CR$_{10}$R$_{20}$)$_t$NR$_{13}$R$_{14}$; especially amino or mono- or di-C$_{1-4}$ alkylamino; (CR$_{10}$R$_{20}$)$_t$S(O)$_m$R$_{18}$, wherein m is 0, 1 or 2; SH; OR$_{11}$; NR$_{10}$C(Z)R$_3$ (such NHCO(C$_{1-10}$ alkyl)); or NR$_{10}$S(O)$_m$R$_8$ (such as NHSO2(C$_{1-10}$ alkyl)).

When A or R$_{22}$ is an (optionally) substituted C$_{3-7}$cycloalkyl group, it is preferably a C$_3$ or C$_6$ ring, most preferably a C$_3$ ring, which ring may be optionally substituted one or more time, preferably 1 to 3 times independently by halogen, such as fluorine, or chlorine; (CR$_{10}$R$_{20}$)$_t$OR$_{11}$; S(O)$_m$R$_{18}$; cyano, (CR$_{10}$R$_{20}$)$_t$NR$_{13}$R$_{14}$, especially amino or mono- or di-C$_{1-4}$ alkylamino; N(R$_{10}$)C(O)X$_1$ and X$_1$ is C$_{1-4}$ alkyl, aryl or arylC$_{1-4}$alkyl; C$_{1-10}$ alkyl, such as methyl, ethyl, propyl, isopropyl, or t-butyl; an optionally substituted alkyl wherein the substituents are halogen, (such as CF$_3$), hydroxy, nitro, cyano, amino, NR$_{13}$R$_{14}$, or S(O)mR$_{18}$; an optionally substituted alkylene, such as ethylene or propylene; an optionally substituted alkyne, such as ethyne; C(O)OR$_{11}$; the group R$_e$; C(O)H; =O; =N—OR$_{11}$; N(H)—OH (or substituted alkyl or aryl derivatives thereof on the nitrogen or the oxime moiety); or N(OR$_d$)—C(O)—R$_f$.

Suitably $R_d$ is hydrogen, a pharmaceutically acceptable cation, aroyl or a $C_{1-10}$ alkanoyl group.

Suitably $R_e$ is a 1,3-dioxyalkylene group of the formula —O—$(CH_2)_s$—O—, wherein s is 1 to 3, preferably s is 2 yielding a 1,3-dioxyethylene moiety, or ketal functionality.

Suitably $R_f$ is $NR_{21}R_{24}$; alkyl$_{1-6}$; halosubstituted alkyl$_{1-6}$; hydroxy substituted alkyl$_{1-6}$; alkenyl$_{2-6}$; aryl or heteroaryl optionally substituted by halogen, alkyl$_{1-6}$, halosubstituted alkyl$_{1-6}$, hydroxyl, or alkoxy$_{1-6}$.

Suitably $R_{21}$ is hydrogen, or alkyl$_{1-6}$.

Suitably $R_{24}$ is hydrogen, alkyl$_{1-6}$, aryl, benzyl, heteroaryl, alkyl substituted by halogen or hydroxyl, or phenyl substituted by a member selected from the group consisting of halo, cyano, alkyl$_{1-6}$, alkoxy$_{1-6}$, halosubstituted alkyl$_{1-6}$. S(O)m alkyl$_{1-6}$; or $R_{21}$ and $R_{24}$ may together with the nitrogen to which they are attached form a ring having 5 to 7 members, which members may be optionally replaced by a heteroatom selected from oxygen, sulfur or nitrogen. The ring may be saturated or contain more than one unsaturated bond. Preferably $R_f$ is $NR_{21}R_{24}$, and more preferably $R_{21}$ and $R_{24}$ are both hydrogen.

When the A or $R_{22}$ optional substituent is $NR_{13}R_{14}$ it is recognized that in some instances this can yield the same moiety as a heterocyclic moiety noted above which is also a suitable variable. Preferably $R_{13}$ and $R_{14}$ are independently hydrogen, $C_{1-4}$ alkyl, preferably methyl, or benzyl.

When the A or $R_{22}$ optional substituent is a C(Z)OR$_{11}$ group, $R_{11}$ is suitably hydrogen, $C_{1-4}$ alkyl, especially methyl.

When the A or $R_{22}$ optional substituent is a $S(O)_mR_{18}$ group, $R_{18}$ is preferably aryl, especially phenyl, or a $C_{1-10}$ alkyl, especially methyl, or ethyl.

When the A or $R_{22}$ optional substituent is a OR$_{11}$ group, $R_{11}$ is preferably hydrogen, aryl, especially phenyl, or $C_{1-10}$ alkyl, especially methyl or ethyl.

When the A or $R_{22}$ optional substituent is a $NHS(O)_2R_{18}$ group, $R_{18}$ is suitably alkyl, especially methyl.

In a preferred subgenus of compounds of Formula (I), $R_1$ is 2-phenoxy-4-pyridyl or 2-phenoxy-4-pyrimidinyl. $R_4$ is phenyl or phenyl substituted one or two times by fluoro, chloro, $C_{1-4}$ alkoxy, —S(O)$_m$ alkyl, methanesulfonamido or acetamido. A is $CH_2OH$, $CH_3$, benzyl, phenyl, $CH_2NH$ (methyl) or $CH_2N$(dimethyl); and $R_{22}$ is methyl, ethyl, methanol, or $CH_2$—O-phenyl; or alternatively the $R_2$ group is 1-hydroxy-3-phenylprop-2-yl, 1-hydroxyprop-2-yl, 1-hydroxybut-2-yl, 1,3-dihydroxyprop-2-yl, or 1-hydroxy-2-phenyethy-2-yl.

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; halosubstituted $C_{1-10}$ alkoxy; S(O)m alkyl, such as methyl thio, methylsulfinyl or methyl sulfonyl; $NR_7R_{17}$, such as amino or mono or disubstituted $C_{1-4}$ alkyl or wherein the $R_7R_{17}$ can cyclize together with the nitrogen to which they are attached to form a 5 to 7 membered ring which optionally contains an additional heteroatom selected from O/N/S; $C_{1-10}$ alkyl, $C_{3-7}$cycloalkyl, or $C_{3-7}$cycloalkyl $C_{1-10}$ alkyl group, such as methyl, ethyl, propyl, isopropyl, t-butyl, etc. or cyclopropyl methyl; halosubstituted $C_{1-10}$ alkyl, such $CF_2CF_2H$, or $CF_3$; an optionally substituted aryl, such as phenyl, or an optionally substituted arylalkyl, such as benzyl or phenethyl, wherein these aryl moieties may also be substituted one to two times by halogen; hydroxy; hydroxy substituted alkyl; $C_{1-10}$ alkoxy; $S(O)_m$alkyl; amino, mono & di-substituted $C_{1-4}$ alkyl amino, such as in the $NR_7R_{17}$ group; $C_{1-4}$ alkyl, or $CF_3$.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid.

In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The term "halo" or "halogens" is used herein to mean the halogens, chloro, fluoro, bromo and iodo.

The term "$C_{1-10}$alkyl" or "alkyl" is used herein to mean both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to cyclopropyl, cyclopentyl, cyclohexyl, and the like.

The term "cycloalkenyl" is used herein to mean cyclic radicals, preferably of 5 to 8 carbons, which have at least one bond including but not limited to cyclopentenyl, cyclohexenyl, and the like.

The term "alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

The term "aryl" is used herein to mean phenyl and naphthyl;

The term "heteroaryl" (on its own or in any combination, such as "heteroaryloxy", or "heteroaryl alkyl") is used herein to mean a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, tetrazole, triazole, imidazole, or benzimidazole.

The term "heterocyclic" (on its own or in any combination, such as "heterocyclylalkyl") is used herein to mean a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydro pyran, or imidazolidine.

The term "aralkyl" or "heteroarylalkyl" or "heterocyclicalkyl" is used herein to mean $C_{1-4}$ alkyl as defined above attached to an aryl, heteroaryl or heterocyclic moiety as also defined herein unless otherwise indicate.

The term "sulfinyl" is used herein to mean the oxide S(O) of the corresponding sulfide, the term "thio" refers to the sulfide, and the term "sulfonyl" refers to the fully oxidized $S(O)_2$ moiety.

The term "aroyl" is used herein to mean C(O)Ar, wherein Ar is as phenyl, naphthyl, or aryl alkyl derivative such as defined above, such group include but are not limited to benzyl and phenethyl.

The term "alkanoyl" is used herein to mean C(O) $C_{1-10}$ alkyl wherein the alkyl is as defined above.

It is recognized that the compounds of the present invention may exist as stereoisomers, regioisomers, or diastereiomers. These compounds may contain one or more asymmetric carbon atoms and may exist in racemic and optically active forms. All of these compounds are included within the scope of the present invention.

Exemplified compounds of Formula (I) include:
1-(1-Hydroxyprop-2-yl)-4-(4-fluorophenyl)-5-[2-(4-fluorophenoxy)pyrimidin-4-yl]imidazole
1-(1,3-Dihydroxyprop-2-yl)-4-(4-fluorophenyl)-5-[2-(4-fluorophenoxy)pyrimidin-4-yl]imidazole
1-(1-Hydroxyprop-2-yl)-4-(4-fluorophenyl)-5-(2-phenoxypyrimidin-4-yl)imidazole
1-(1-Phenoxyprop-2-yl)$_4$-(4-fluorophenyl)-5-(2-phenoxypyrimidin-4-yl)imidazole
1-(1-Hydroxy-3-phenylprop-2-yl)-4-(4-fluorophenyl)-5-(2-phenoxypyrimidin-4-yl)imidazole
1-(-Hydroxybut-2-yl)-4(4-fluorophenyl)-5-(2-phenoxypyrimidin-4-yl)imidazole
1-(1,3-Dihydroxyprop-2-yl)-4-(4-fluorophenyl)-5-(2-phenoxypyrimidin-4-yl)imidazole
1-(1-Hydroxy-2-phenyleth-2-yl)-4-(4-fluorophenyl)-5-(2-phenoxypyrimidin-4-yl)imidazole
1-(1-Hydroxyprop-2-yl)-4-(4-fluorophenyl)-5-[2-(4-chlorophenoxy)pyrimidin-4-yl]imidazole
1-(1-Hydroxybut-2-yl)-4-(4-fluorophenyl)-5-[2-(4-chlorophenoxy)pyrimdin-4-yl]imidazole
1-(1-Hydroxyprop-2-yl)-4-(4-fluorophenyl)-5-[2-(4-methylphenoxypyrimidin-4-yl]imidazole
1-(1-Hydroxybut-2-yl)-4-(4-fluorophenyl)-5-[2-(4-methylphenoxy)pyrimidin-4-yl]imidazole
1-(1,3-Dihydroxyprop-2-yl)-4-(4-fluorophenyl)-5-[2-(4-methylphenoxy)pyrimidin-4-yl]imidazole
1-(4-N-Morpholinyl-2-but-yl)-4-(4-fluorophenyl)-5-(2-phenoxypyrimidiny-4-yl)imidazole The compounds of Formula (I) may be obtained by applying synthetic procedures, some of which are illustrated in Schemes I to XII herein. The synthesis provided for in these Schemes is applicable for the producing compounds of Formula (I) having a variety of different $R_1$, $R_2$, and $R_4$ groups which are reacted, employing optional substituents which are suitably protected, to achieve compatibility with the reactions outlined herein. Subsequent deprotection, in those cases, then affords compounds of the nature generally disclosed. While the schemes describe compounds of Formula (I) with Y as oxygen, one skilled in the art would readily be able to make compounds of Formula (I) wherein Y is sulfur using similar reaction processes as exemplified herein.

Once the imidazole nucleus has been established, further compounds of Formula (I) may be prepared by applying standard techniques for functional group interconversion, well known in the art. For instance: $C(O)NR_{13}R_{14}$ from $CO_2CH_3$ by heating with or without catalytic metal cyanide, e.g. NaCN, and $HNR_{13}R_{14}$ in $CH_3OH$; $OC(O)R_3$ from OH with e.g., $ClC(O)R_3$ in pyridine; $NR_{10}$—$C(S)NR_{13}R_{14}$ from $NHR_{10}$ with an alkylisothiocyante or thiocyanic acid; $NR_6C(O)OR_6$ from $NHR_6$ with the alkyl chloroformate; $NR_{10}C(O)NR_{13}R_{14}$ from $NHR_{10}$ by treatment with an isocyanate, e.g. HN=C=O or $R_{10}N$=C=O; $NR_{10}$—$C(O)R_8$ from $NHR_{10}$ by treatment with Cl—$C(O)R_3$ in pyridine; $C(=NR_{10})NR_{13}R_{14}$ from $C(NR_{13}R_{14})SR_3$ with $H_3NR_3{}^+OAc^-$ by heating in alcohol; $C(NR_{13}R_{14})SR_3$ from $C(S)NR_{13}R_{14}$ with $R_6$—I in an inert solvent, e.g. acetone; $C(S)NR_{13}R_{14}$ (where $R_{13}$ or $R_{14}$ is not hydrogen) from $C(S)NH_2$ with $HNR_{13}R_{14}$— $C(=NCN)$—$NR_{13}R_{14}$ from $C(=NR_{13}R_{14})$—$SR_3$ with $NH_2CN$ by heating in anhydrous alcohol, alternatively from $C(=NH)$—$NR_{13}R_{14}$ by treatment with BrCN and NaOEt in EtOH; $NR_{10}$—$C(=NCN)SR_8$ from $NHR_{10}$ by treatment with $(R_8S)_2C$=NCN; $NR_{10}SO_2R_3$ from $NHR_{10}$ by treatment with $ClSO_2R_3$ by heating in pyridine; $NR_{10}C(S)R_3$ from —$NR_{10}C(O)R_8$ by treatment with Lawesson's reagent [2,4-bis(4-methoxyphenyl)-1,3,2,4-dithiadiphosphetane-2,4-disulfide]; $NR_{10}SO_2CF_3$ from $NHR_6$ with triflic anhydride and base wherein $R_3$, $R_6$, $R_{10}$, $R_{13}$ and $R_{14}$ are as defined in Formula (I) herein.

Precursors of the groups $R_1$, $R_2$ and $R_4$ can be other $R_1$, $R_2$ and $R_4$ groups which can be interconverted by applying standard techniques for functional group interconversion. For example a compound of the formula (I) wherein $R_2$ is halo substituted $C_{1-10}$ alkyl can be converted to the corresponding $C_{1-10}$ alkyl$N_3$ derivative by reacting with a suitable azide salt, and thereafter if desired can be reduced to the corresponding $C_{1-10}$alkyl $NH_2$ compound, which in turn can be reacted with $R_{18}S(O)_2X$ wherein X is halo (e.g., chloro) to yield the corresponding $C_{1-10}$alkyl $NHS(O)_2R_{18}$ compound.

Alternatively a compound of the formula (I) where $R_2$ is halo-substituted $C_{1-10}$-alkyl can be reacted with an amine $R_{13}R_{14}NH$ to yield the corresponding $C_{1-10}$-alkyl $NR_{13}R_{14}$ compound, or can be reacted with an alkali metal salt of $R_{18}SH$ to yield the corresponding $C_{1-10}$alkyl$SR_{18}$ compound.

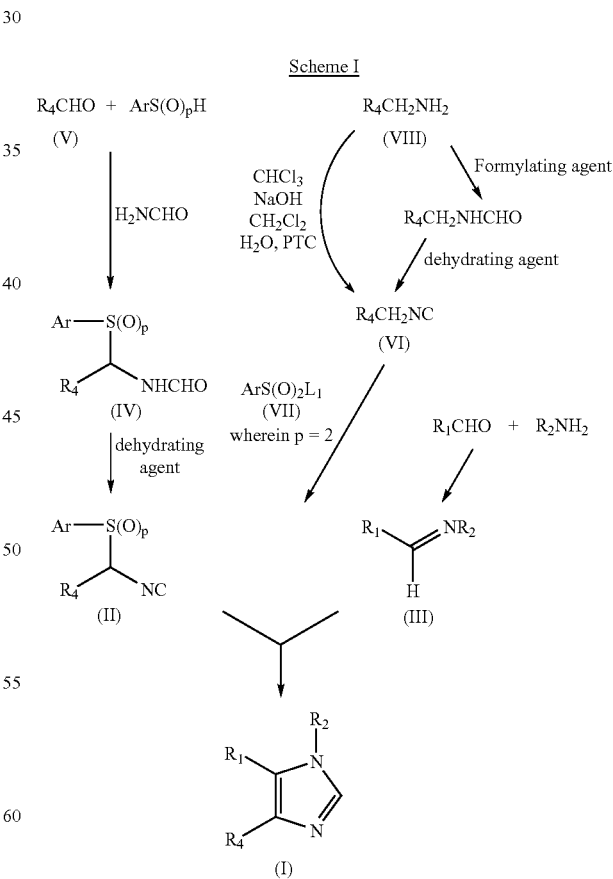

Scheme I

Referring to Scheme I the compounds of Formula (I) are suitably prepared by reacting a compound of the Formula (II) with a compound of the Formula (III) wherein p is 0 or 2, $R_1$, $R_2$ and $R_4$ are as defined herein, for Formula (I), or are precursors of the groups $R_1$, $R_2$ and $R_4$, and Ar is an optionally substituted phenyl group, and thereafter if necessary converting a precursor of $R_1$, $R_2$ and $R_4$ to a group $R_1$, $R_2$ and $R_4$. It is recognized that $R_2NH_2$ which is reacted with $R_1CHO$ to form the imine, Formula (III) the $R_2$ moiety when it contains a reactive functional group, such as a primary or secondary amine, an alcohol, or thiol compound the group must be suitably protected. Suitable protecting groups may be found in, Protecting Groups in Organic Synthesis, Greene T W, Wiley-Interscience, New York, 1981, whose disclosure is incorporated herein by reference. For instance, when $R_2$ is a heterocyclic ring, such as a piperidine ring, the nitrogen is protected with groups such as t-Boc, $CO_2R_{18}$, or a substituted arylalkyl moiety.

Suitably, the reaction is performed at ambient temperature or with cooling (e.g. −50° to 10°) or heating in an inert solvent such as methylene chloride, DMF, tetrahydrofuran, toluene, acetonitrile, or dimethoxyethane in the presence of an appropriate base such as $K_2CO_3$, t-bu$NH_2$, 1,8-diazabicyclo [5.4.0.] undec-7-ene (DBU), or a guanidine base such as 1,5,7-triaza-bicyclo [4.4.0] dec-5-ene (TBD). The intermediates of formula (II) have been found to be very stable and capable of storage for a long time. Preferably, p is 2. PTC is defined as a phase transfer catalyst for use herein.

Compounds of the Formula (II) have the structure:

(II)

wherein p is 0, or 2; $R_4$ is as defined for Formula (I) and Ar is an optionally substituted aryl as defined herein. Suitably, Ar is phenyl optionally substituted by $C_{1-4}$alkyl, $C_{1-4}$ alkoxy or halo. Preferably Ar is phenyl or 4-methylphenyl, i.e. a tosyl derivative.

Reaction a compound of the Formula (II) wherein p=2, with a compound of the Formula (III)—Scheme I gives consistently higher yields of compounds of Formula (I) than when p=0. In addition, the reaction of Formula (II) compounds wherein p=2 is more environmentally and economically attractive. When p=0, the preferred solvent used is methylene chloride, which is environmentally unattractive for large scale processing, and the preferred base, TBD, is also expensive, and produces some byproducts and impurities, than when using the commercially attractive synthesis (p=2) as further described herein.

As noted, Scheme I utilizes the 1,3-dipolar cycloadditions of an anion of a substituted aryl thiomethylisocyanide (when p=0) to an imine. More specifically, this reaction requires a strong base, such as an amine base, to be used for the deprotonation step. The commercially available TBD is preferred although t-butoxide, Li+ or Na+, or K+ hexamethyldisilazide may also be used. While methylene chloride is the prefered solvent, other halogenated solvents, such as chloroform or carbon tetrachloride; ethers, such as THF, DME, DMF, diethylether, t-butyl methyl ether; as well as acetonitrile, toluene or mixtures thereof can be utiltized. The reaction may take place from about −20° C. to about; 40° C., preferably from about 0° C. to about 23° C., more preferably from about 0° C. to about 10° C., and most preferably about 4° C. for reactions involving an $R_1$ group of pyrimidine. For compounds wherein $R_1$ is pyridine, it is recognized that varying the reations conditions of both temperature and solvent may be necessary, such as decreasing temperatures to about −50° C. or changing the solvent to THF.

In a further process, compounds of Formula (I) may be prepared by coupling a suitable derivative of a compound of Formula (IX):

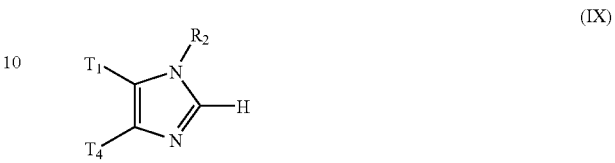

(IX)

wherein $T_1$ is hydrogen and $T_4$ is $R_4$, or alternatively $T_1$ is $R_1$ and $T_4$ is H in which $R_1$, $R_2$ and $R_4$ are as hereinbefore defined; with: (i) when $T_1$ is hydrogen, a suitable derivative of the heteroaryl ring $R_1H$, under ring coupling conditions, to effect coupling of the heteroaryl ring $R_1$ to the imidazole nucleus at position 5; (ii) when $T_4$ is hydrogen, a suitable derivative of the aryl ring $R_4H$, under, ring coupling conditions, to effect coupling of the aryl ring $R_4$ to the imidazole nucleus at position 4.

Such aryl/heteroaryl coupling reactions are well known to those skilled in the art. In general, an organometallic synthetic equivalent of an anion of one component is coupled with a reactive derivative of the second component, in the presence of a suitable catalyst. The anion equivalent may be formed from either the imidazole of Formula (IX), in which case the aryl/heteroaryl compound provides the reactive derivative, or the aryl/heteroaryl compound in which case the imidazole provides the reactive derivative. Accordingly, suitable derivatives of the compound of Formula (IX) or the aryl/heteroaryl rings include organometallic derivatives such as organomagnesium, organozinc, organostannane and boronic acid derivatives and suitable reactive derivatives include the bromo, iodo, fluorosulfonate and trifluoromethanesulphonate derivatives. Suitable procedures are described in WO 91/19497, the disclosure of which is incorporated by reference herein.

Suitable organomagnesium and organozinc derivatives of a compound of Formula (IX) may be reacted with a halogen, fluorosulfonate or triflate derivative of the heteroaryl or aryl ring, in the presence of a ring coupling catalyst, such as a palladium (O) or palladium (II) catalyst, following the procedure of Kumada et al., Tetrahedron Letters, 22, 5319 (1981). Suitable such catalysts include tetrakis-(triphenylphosphine)palladium and $PdCl_2$[1,4-bis-(diphenylphosphino)-butane], optionally in the presence of lithium chloride and a base, such as triethylamine. In addition, a nickel (II) catalyst, such as Ni(II) $Cl_2$(1,2-biphenylphosphino) ethane, may also be used for coupling an aryl ring, following the procedure of Pridgen et al., J. Org. Chem, 1982, 47, 4319. Suitable reaction solvents include hexamethylphosphor-amide. When the heteroaryl ring is 4-pyridyl, suitable derivatives include 4-bromo- and 4-iodo-pyridine and the fluorosulfonate and triflate esters of 4-hydroxy pyridine. Similarly, suitable derivatives for when the aryl ring is phenyl include the bromo, fluorosulfonate, triflate and, preferably, the iodo-derivatives. Suitable organomagnesium and organozinc derivatives may be obtained by treating a compound of Formula (IX) or the bromo derivative thereof with an alkyllithium compound to yield the corresponding lithium reagent by deprotonation or transmetallation, respectively. This lithium intermediate may then be treated with an excess of a magnesium halide or zinc halide to yield the corresponding organometallic reagent.

A trialkyltin derivative of the compound of Formula (IX) may be treated with a bromide, fluorosulfonate, triflate, or, preferably, iodide derivative of an aryl or heteroaryl ring compound, in an inert solvent such as tetrahydrofuran, preferably containing 10% hexamethylphosphoramide, in the presence of a suitable coupling catalyst, such as a palladium (0) catalyst, for instance tetrakis-(triphenylphosphine)palladium, by the method described in by Stille, J. Amer. Chem. Soc, 1987, 109, 5478, U.S. Pat. Nos. 4,719,218 and 5,002,941, or by using a palladium (H) catalyst in the presence of lithium chloride optionally with an added base such as triethylamine, in an inert solvent such as dimethyl formamide. Trialkyltin derivatives may be conveniently obtained by metallation of the corresponding compound of Formula (IX) with a lithiating agent, such as s-butyl-lithium or n-butyllithium, in an ethereal solvent, such as tetrahydrofuran, or treatment of the bromo derivative of the corresponding compound of Formula (IX) with an alkyl lithium, followed, in each case, by treatment with a trialkyltin halide. Alternatively, the bromo-derivative of a compound of Formula (IX) may be treated with a suitable heteroaryl or aryl trialkyl tin compound in the presence of a catalyst such as tetrakis-(triphenyl-phosphine)palladium, under conditions similar to those described above.

Boronic acid derivatives are also useful. Hence, a suitable derivative of a compound of Formula (IX), such as the bromo, iodo, triflate or fluorosulphonate derivative, may be reacted with a heteroaryl- or aryl-boronic acid, in the presence of a palladium catalyst such as tetrakis-(triphenylphosphine)-palladium or PdCl$_2$ [1,4-bis-(diphenyl-phosphino) butane] in the presence of a base such as sodium bicarbonate, under reflux conditions, in a solvent such as dimethoxyethane (see Fischer and Hayiniga, Rec. Trav. Chim. Pays Bas, 84, 439, 1965, Snieckus, V., Tetrahedron Lett., 29, 2135, 1988 and Terashimia, M., Chem. Pharm. Bull., 11, 4755, 1985). Non-aqueous conditions, for instance, a solvent such as DMF, at a temperature of about 100° C., in the presence of a Pd(II) catalyst may also be employed (see Thompson W J et al, J Org Chem, 49, 5237, 1984). Suitable boronic acid derivatives may be prepared by treating the magnesium or lithium derivative with a trialkylborate ester, such as triethyl, tri-iso-propyl or tributylborate, according to standard procedures.

In such coupling reactions, it will be readily appreciated that due regard must be exercised with respect to functional groups present in the compounds of Formula (IX)., Thus, in general, amino and sulfur substituents should be non-oxidised or protected.

Compounds of Formula (IX) are imidazoles and may be obtained by any of the procedures herein before described for preparing compounds of Formula (I). In particular, an a-halo-ketone or other suitably activated ketones R$_4$COCH$_2$Hal (for compounds of Formula (IX) in which T$_1$ is hydrogen) or R$_1$COCH$_2$Hal (for compounds of Formula (IX) in which T$_4$ is hydrogen) may be reacted with an amidine of the formula R$_2$NH—C=NH, wherein R$_2$ is as defined in Formula (I), or a salt thereof, in an inert solvent such as a halogenated hydrocarbon solvent, for instance chloroform, at a moderately elevated temperature, and, if necessary, in the presence of a suitable condensation agent such as a base. The preparation of suitable a-halo-ketones is described in WO 91/19497. Suitable reactive esters include esters of strong organic acids such as a lower alkane sulphonic or aryl sulphonic acid, for instance, methane or p-toluene sulphonic acid. The amidine is preferably used as the salt, suitably the hydrochloride salt, which may then be converted into the free amidine in situ, by employing a two phase system in which the reactive ester is in an inert organic solvent such as chloroform, and the salt is in an aqueous phase to which a solution of an aqueous base is slowly added, in dimolar amount, with vigorous stirring. Suitable amidines may be obtained by standard methods, see for instance, Garigipati R, Tetrahedron Letters, 190, 31, 1989.

Compounds of Formula (I) may also be prepared by a process which comprises reacting a compound of Formula (IX), wherein T$_1$ is hydrogen, with an N-acyl heteroaryl salt, according to the method disclosed in U.S. Pat. No. 4,803,279, U.S. Pat. No. 4,719,218 and U.S. Pat. No. 5,002,941, to give an intermediate in which the heteroaryl ring is attached to the imidazole nucleus and is present as a 1,4-dihydro derivative thereof, which intermediate may then be subjected to oxidative-deacylation conditions (Scheme II). The heteroaryl salt, for instance a pyridinium salt, may be either preformed or, more preferably, prepared in situ by adding a substituted carbonyl halide (such as an acyl halide, an aroyl halide, an aryialkyl haloformate ester, or, preferably, an alkyl haloformate ester, such as acetyl bromide, benzoylchloride, benzyl chloroformate, or, preferably, ethyl chloroformate) to a solution of the compound of Formula (DC) in the heteroaryl compound R$_1$H or in an inert solvent such as methylene chloride to which the heteroaryl compound has been added. Suitable deacylating and oxidising conditions are described in U.S. Pat. Nos. 4,803,279, 4,719,218 and 5,002,941, which references are hereby incorporated by reference in their entirety. Suitable oxidizing systems include sulfur in an inert solvent or solvent mixture, such as decalin, decalin and diglyme, p-cymene, xylenc or mesitylene, under reflux conditions, or, preferably, potassium t-butoxide in t-butanol with dry air or oxygen.

Scheme II

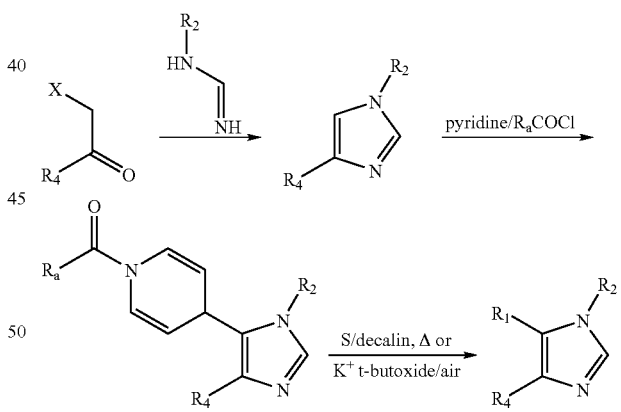

In a further process, illustrated in Scheme III below, compounds of Formula (I) may be prepared by treating a compound of Formula (X) thermally or with the aid of a cyclising agent such as phosphorus oxychloride or phosphorus pentachloride (see Engel and Steglich, Liebigs Ann Chem, 1978, 1916 and Strzybny et al., J Org Chem, 1963, 28, 3381). Compounds of Formula (X) may be obtained, for instance, by acylating the corresponding a-keto-amine with an activated formate derivative such as the corresponding anhydride, under standard acylating conditions followed by formation of the imine with R$_2$NH$_2$. The aminoketone may be derived from the parent ketone by examination and reduction and the requisite ketone may in turn be prepared by decarboxylation of the beta-ketoester obtained from the condensation of an aryl (heteroaryl) acetic ester with the R₁COX component.

Scheme IIII

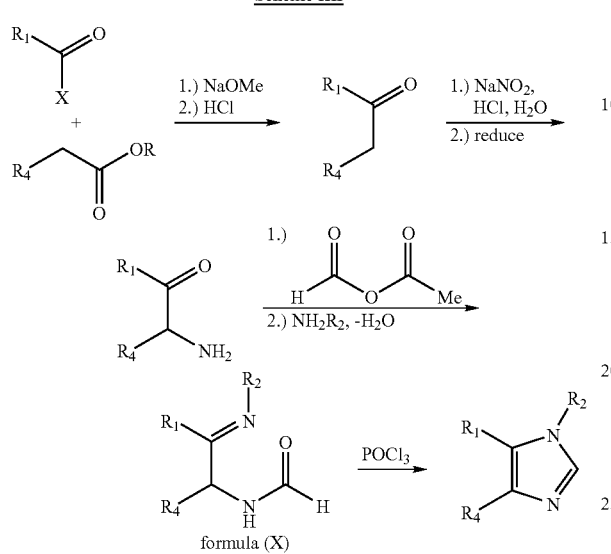

In Scheme IV illustrated below, two (2) different routes which use ketone (formula XI) for preparing a compound of Formula (I). A heterocyclic ketone (XI) is prepared by adding the anion of the alkyl heterocycle such as 4-methylquinoline (prepared by treatment thereof with an alkyl lithium, such as n-butyl lithium) to an N-alkyl-O-alkoxybenzamide, ester, or any other suitably activated derivative of the same oxidation state. Alternatively, the anion may be condensed with a benzaldehyde, to give an alcohol which is then oxidised to the ketone (XI).

wherein R₄ is as hereinbefore defined, or (b) an excess of an acyl halide, for instance an acyl chloride, of the Formula (XIV):

R₄COHal      (XIV)

wherein R₄ is as hereinbefore defined and Hal is halogen, or a corresponding anhydride, to give a bis-acylated intermediate which is then treated with a source of ammonia, such as ammonium acetate.

Scheme V

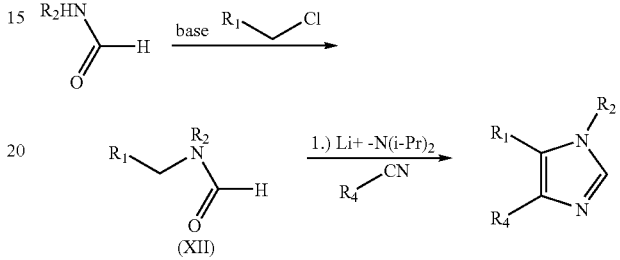

One variation of this approach is illustrated in Scheme V above. A primary amine (R₂NH₂) is treated with a halomethyl heterocycle of Formula R₁ CH₂X to give the secondary amine which is then converted to the amide by standard techniques. Alternatively the amide may be prepared as illustrated in scheme V by alkylation of the formamide with R₁CH₂X. Deprotonation of this amide with a strong amide base, such as lithium di-iso-propyl amide or sodium bis (trimethylsilyl)amide, followed by addition of an excess of an aroyl chloride yields the bis-acylated compound which is then closed to an imidazole compound of Formula (I), by heating in acetic acid containing ammonium acetate. Alter- Scheme IV

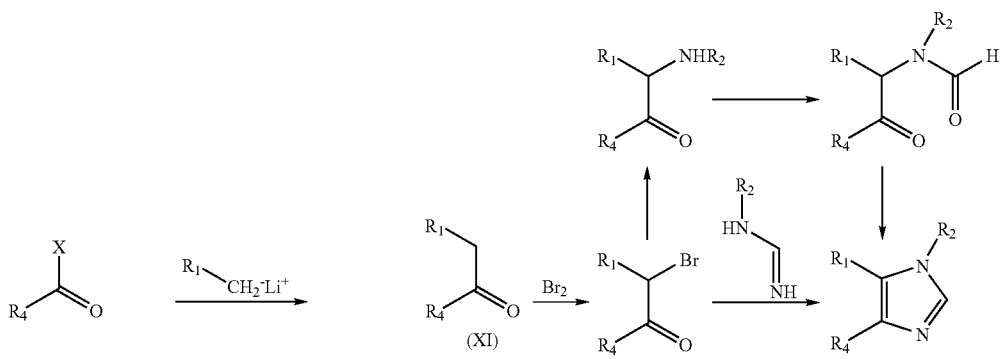

In a further process, N-substituted compounds of Formula (I) may be prepared by treating the anion of an amide of Formula (XII):

R₁CH₂NR₂COH      (XII)

wherein R₁ and R₂ with:

(a) a nitrile of the Formula (XIII):

R₄CN      (XIII)

natively, the anion of the amide may be reacted with a substituted aryl nitrile to produce the imidazole of Formula (I) directly.

The following description and schemes are further exemplification of the process as previously described above in Scheme I. Various pyrimidine aldehyde derivatives 6, as depicted in Scheme VI below, can be prepared by modification of the procedures of Bredereck et al. (*Chem. Ber.* 1964, 97, 3407) whose disclosure is incorporated by reference herein. These pyrimidine aldehydes are then utilized as intermediates in the synthesis as further described herein.

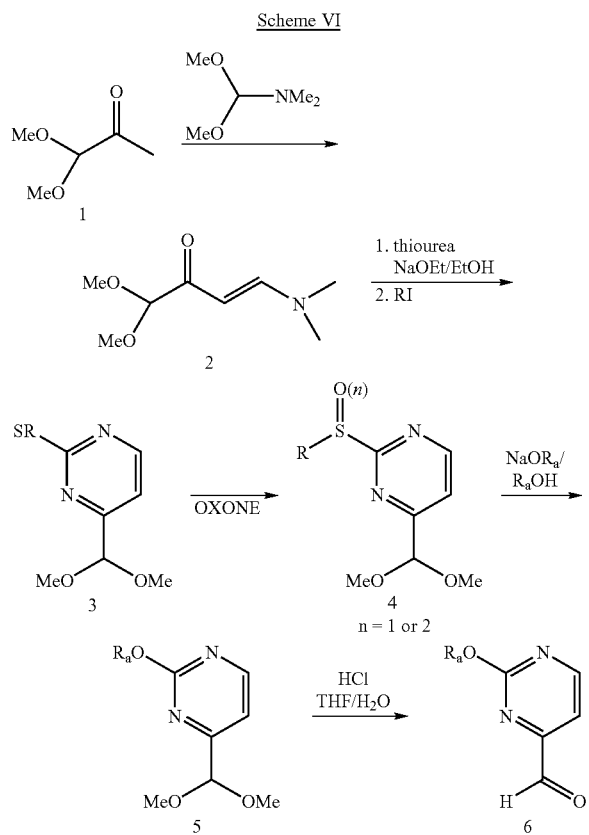

The reaction of imines with tosylmethyl isonitriles was first reported by van Leusen (van Leusen, et al., *J. Org. Chem.* 1977, 42, 1153.) Reported were the following conditions: tert butyl amine(tBuNH$_2$) in dimethoxyethane (DME), K$_2$CO$_3$ in MeOH, and NaH in DME. Upon re-examination of these conditions each was found to produce low yields. A second pathway involving amine exchange to produce the t-butyl imine followed by reaction with the isocyanide to produce a I-tBu imidazole was also operating. This will likely occur using any primary amine as a base.

The secondary amines, while not preferred may be used, but may also decompose the isonitrile slowly. Reactions will likely require about 3 equivalents of amine to go to completion, resulting in approximately 50% isolated yields. Hindered secondary amines (diisopropylamine) while usable are very slow and generally not too effective. Use of tertiary and aromatic amines, such as pyridine, and triethylamine gave no reaction under certain test conditions, but more basic types such as DBU, and 4-dimethylamino pyridine (DMAP) while slow, did produce some yields and hence may be suitable for use herein.

As depicted in Schemes VII and VIII below, the pyrimidine aldehydes of Scheme VI, can be condensed with a primary amine, to generate an imine, which may suitably be isolated or reacted in situ, with the desired isonitrile in the presence of a variety of suitable bases, and solvents as described herein to afford the 5-(4-pyrimidinyl)-substituted imidazoles, wherein R$_2$ and R$_4$ are as defined herein for Formula (I) compounds.

One preferred method for preparing compounds of Formula (I) is shown below in Scheme VII, in which the imine is prepared and isolated in a separate step prior to the addition of the isonitrile. The yield for making the imines varied, and environmentally less-acceptable solvents, such as CH$_2$Cl$_2$ were often used in their preparation.

This reaction, wherein p=2, requires a suitable base for the reaction to proceed. The reaction requires a base strong enough to deprotonate the isonitrile. Suitable bases include an amine, a carbonate, a hydride, or an alkyl or aryl lithium reagent; or mixtures thereof. Bases include, but are not limited to, potassium carbonate, sodium carbonate, primary and secondary amines, such as t-butylamine, diisopropyl amine, morpholine, piperidine, pyrrolidine, and other non-nucleophilic bases, such as DBU, DMAP and 1,4-diazabicyclo[2.2.2]octane (DABCO).

Suitable solvents for use herein, include but are not limited to the organic solvents of N,N-dimethyl-formamide (DMF), MeCN, halogenated solvents, such as methylene chloride or chloroform, tetrahydrofuran (THF), dimethyl-sulfoxide (DMSO), alcohols, such as methanol or ethanol, benzene, toluene, DME or EtOAc. Preferably the solvent is DMF, DME, THF, or MeCN, more preferably DMF. Product isolation may generally be accomplished by adding water and filtering the product as a clean compound. In scheme VII below, Ra is as defined for Formula (I) compounds, and X is oxygen or sulfur.

Scheme VII

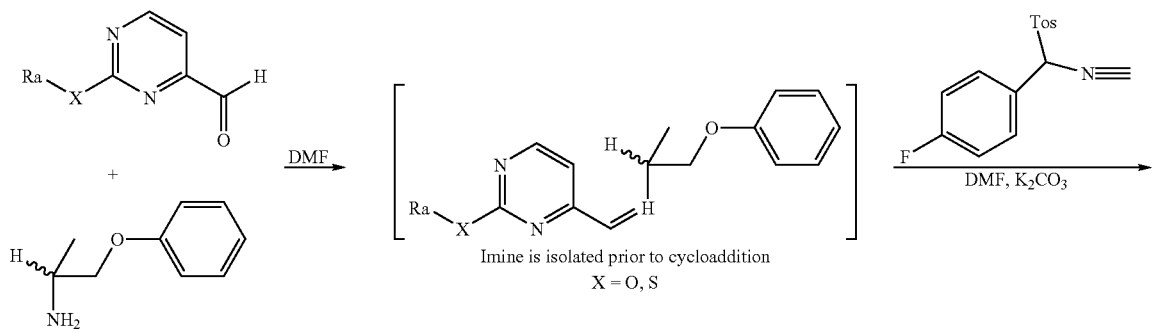

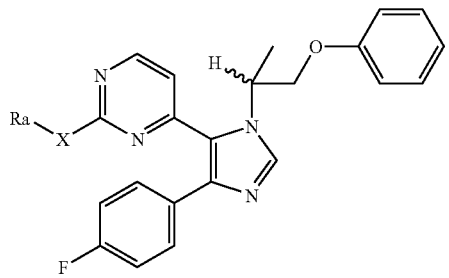

While not convenient for large scale work, addition of NaH to the isonitrile, perhaps with temperatures lower than 25° C. (in THF) are likely needed. Additionally, BuLi has also been reported to be an effective base for deprotonating tosyl benzylisonitriles at −50° C. (DiSanto, et al., *Synth. Commun.* 1995, 25, 795).

Various temperature conditions may be utilized depending upon the preferred base. For instance, tBuNH$_2$/DME, K$_2$CO$_3$/MeOH, K$_2$CO$_3$ in DMF, at temperatures above 40° C., the yields may drop to about 20% but little difference is expected between 0° C. and 25° C. Consequently, temperature ranges below 0° C., and above 80° C. are contemplated as also being within the scope of this invention. Preferably, the temperature ranges are from about 0° C. to about 25° C. For purposes herein, room temperature, is generally depicted as 25° C., but it is recognized that this may vary from 20° C. to 30° C.

As shown in Scheme VIII below, the imine is preferably formed in situ in a solvent. This preferred synthesis, is a process which occurs as a one-pot synthesis. Suitably, when the primary amine is utilized as a salt, such as in the dihydrochloride salt in the Examples, the reaction may further include a base, such as potassium carbonate, prior to the addition of the isonitrile. For hydroxy-containing amines a protected group(PG) may be required in the imine forming and cycloaddition reactions; suitably the PG is silyl (such as triethyl, diphenyl-t-butyl, dimethyl-t-butyl) or C(O)$_2$R, wherein R is preferably alkyl, aryl, arylalkyl moieties well known to those skilled in the art. Reaction conditions, such as solvents, bases, temperatures, etc. are similar to those illustrated and discussed above for the isolated imine as shown in Scheme VII. One skilled in the art would readily recognize that under some circumstances, the in situ formation of the imine may require dehydrating conditions, or may require acid catalysis.

Scheme VIII

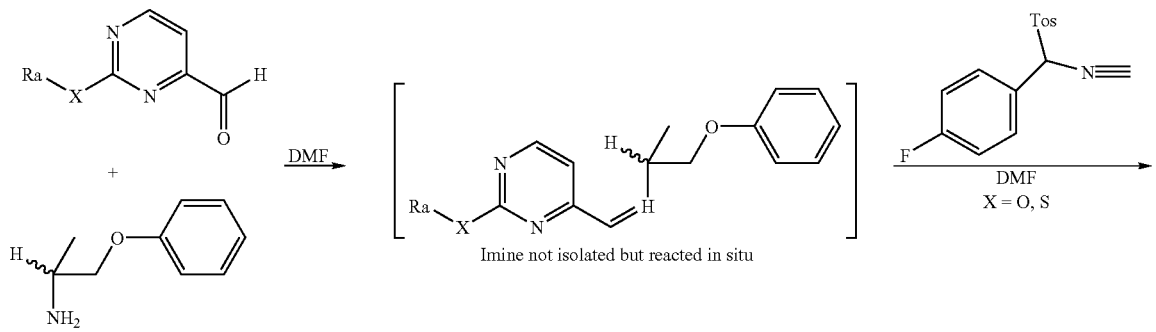

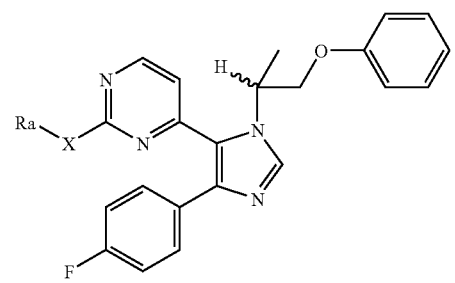

Scheme IX, describes an alternative process for making compounds of formula (I). In this particular instance, the alkylthio moiety is oxidized to the methyl sulfinyl or sulfonyl moiety which is reacted with a suitable YR$_a$ moiety.

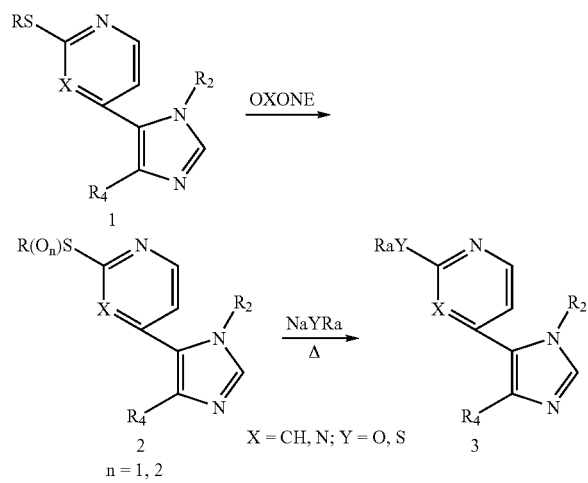

Another embodiment of the present invention is the novel hydrolysis of 2-thioalkylpyrimidine acetal to 2-thioalkylpyrimidine aldehyde, as shown in Scheme X below. Hydrolysis of the acetal to aldehyde using various known reaction conditions, such as formic acid, did not produce a satisfactory yield of the aldehyde, <13% was obtained. The preferred synthesis involves the use of AcOH (fresh) as solvent and con-centrated H$_2$SO$_4$ under heating conditions, preferably a catalytic amount of sulfuric acid. Heating conditions include temperatures from about 60 to 85° C., preferably from about 70 to about 80° C. as higher temperatures show a darkening of the reaction mixture. After the reaction is completeed the mixture is cooled to about room temperature and the acetic acid is removed. A more preferred alternative procedure to this involves heating the acetal in 3N HCl at 40° C. for about 18 hours, cooling and extracting the bicarbonate neutralized solution into EtOAc

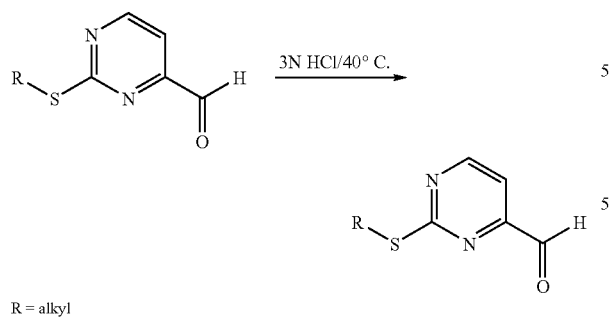

The final 2-(RaY)pyrimidin-4-ylimidazole compounds of Formula (I), as well as similar pyridine containing compounds can be prepared by one of three methods: 1) direct reaction of the 2-(RaY)pyrimidine imine with the isonitrile; 2) oxidation of the 2-alkylthiopyrimidine derivative to the corresponding sulfoxide followed by displacement with the desired HYRa under basic conditions, for example using a metal salt of HYRa or in the presence of a non-nucleophilic amine or alkali metal base; or 3) reaction of the 2-halopyrimidine or pyridine imine with the isonitrile followed by displacement with HYRa under basic conditions described in the second method, see also Adams et al., U.S. Ser. No. 08/659,102 filed 3 Jun. 1996, Scheme XI, whose disclosure is incorporated herein by reference in its entirety.

While these schemes herein are presented, for instance, with R$_{22}$=CH$_2$OPh and (A)=methyl in the R$_2$ position, and 4-fluorophenyl for R$_4$, any suitable R$_2$ moiety or R$_4$ moiety may be added in this manner if it can be prepared on the primary amine. Similarly, any suitable R$_4$ can be added via the isonitrile route.

The compounds of Formula (II), in Scheme I, may be prepared by the methods of van Leusen et al., supra. For example, a compound of the Formula (II) may be prepared by dehydrating a compound of the Formula (IV)—Scheme I, wherein Ar, R$_4$ and p are as defined herein.

Suitable dehydrating agents include phosphorus oxychloride, oxalyl chloride, thionyl chloride, phosgene, or tosyl chloride in the presence of a suitable base such as triethylamine or diisopropylethylamine, or similar bases, etc. such as pyridine.

Suitable solvents are dimethoxy ether, tetrahydrofuran, or halogenated solvents, preferably THF. The reaction is most efficent when the reaction temperatures are kept between −10° C. and 0° C. At lower temperatures incomplete reaction occurs and at higher temperatures, the solution turns dark and the product yield drops.

The compounds of formula (IV)—Scheme I may be prepared by reacting a compound of the formula (V) Scheme I, R$_4$CHO where R$_4$ is as defined herein, with ArS(0)$_p$H and formamide with or without water removal, preferably under dehydrating conditions, at ambient or elevated temperature e.g. 30° to 150°, conveniently at reflux, optionally in the presence of an acid catalyst. Alternatively trimethysilylchloride can be used in place of the acid catalyst. Examples of acid catalysts include camphor-10-sulphonic acid, formic acid, p-toluenesulphonic acid, hydrogen chloride or sulphuric acid.

An optimal method of making an isonitrile of Formula (II) is illustrated below, in Scheme XI.

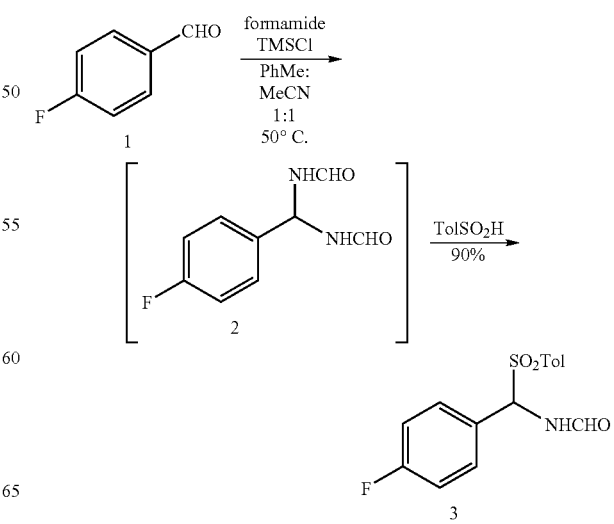

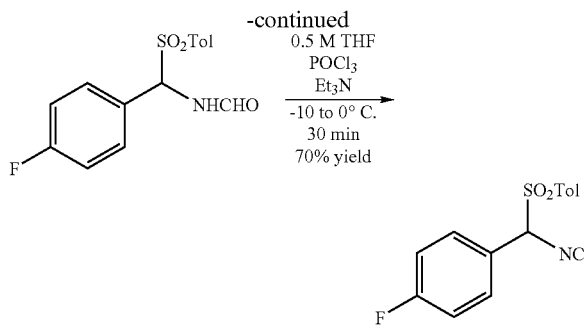

The conversion of the substituted aldehyde to the tosylbenzyl formamide may be accomplished by heating the aldehyde, 1-Scheme XI, with an acid, such as p-toluenesulfonic acid, formic acid or camphorsulfonic acid; with formamide and p-toluene-sulfinic acid [under reaction conditions of about 60° C. for about 24 hours].

Preferably, no solvent is used. The reaction, may give poor yields (<30%) when solvents, such as DMF, DMSO, toluene, acetonitrile, or excess formamide are used. Temperatures less than 60° C. are generally poor at producing the desired product, and temperatures in excess of 60° C. may produce a product which decomposes, or obtain a benzylic bis-formamide, 2-Scheme XI.

Another embodiment of the present invention is the synthesis of the tosyl benzyl formamide compound, achieved by reacting the bisformamide intermediate, 2-Scheme XI with p-toluenesulfinic acid. In this preferred route, preparation of the bis-formamide from the aldehyde is accomplished by heating the aldehyde with formamide, in a suitable solvent with acid catalysis. Suitable solvents are toluene, acetonitrile, DMF, and DMSO or mixtures thereof. Acid catalysts, are those well known in the art, and include but are not limited to hydrogen chloride, p-toluene-sulfonic acid, camphorsulfonic acid, and other anhydrous acids. The reaction can be conducted at temperatures ranging from about 25° C. to 110° C., preferably about 50° C., suitably for about 4 to about 5 hours, longer reaction times are also acceptable. Product decomposition and lower yields may be observed at higher temperatures (>70° C.) at prolonged reactions times. Complete conversion of the product generally requires water removal from the reaction mixture.

Preferred conditions for converting a bis-formamide derivative to the tosyl benzyl formamide are accomplished by heating the bisformamide in a suitable solvent with an acid catalyst and p-toluenesulfinic acid. Solvents for use in this reaction include but are not limited to toluene, and acetonitrile or mixtures thereof.

Additional mixtures of these solvents with DMF, or DMSO may also be used but may result in lower yields. Temperatures may range from about 30° C. to about 100° C. Temperatures lower than 40° C. and higher than 60° C. are not preferred as the yield and rate decreases. Preferably the range is from about 40 to 60° C., most preferably about 50° C. The optimal time is about 4 to 5 hours, although it may be longer. Preferably, acids used include but are not limited to, toluenesulfonic acid, camphorsulfonic acid, and hydrogen chloride and other anhydrous acids. Most preferably the bisformamide is heated in toluene:acetonitrile in a 1:1 ratio, with p-toluenesulfinic acid and hydrogen chloride.

Another embodiment of the present invention is the preferred synthetic route for synthesis of the tosylbenzyl formamide compound which is accomplished using a one-pot procedure. This process first converts the aldehyde to the bis-formamide derivative and subsequently reacts the bis-formamide derivative with toluenesulfinic acid. This procedure combines the optimized conditions into a single, efficient process. High yields, >90% of the aryl benzylformamide may be obtained in such a manner.

Preferred reaction conditions employ a catalyst, such as trimethylsilyl chloride (TMSCl), in a preferred solvent, toluene:acetonitrile, preferably in a 1:1 ratio. A reagent, such as TMSCl, is preferred which reacts with water produced therein and at the same time produces hydrogen chloride to catalyze the reaction. Also preferred is use of hydrogen chloride and p-toluenesulfonic acid. Therefore, three suitable reaction conditions for use herein include 1) use of a dehydrating agent which also provides hydrogen chloride, such as TMSCl; or by 2) use of a suitable dehydrating agent and a suitable source of acid source, such as but not limited to, camphorsulfonic acid, hydrogen chloride or toluenesulfonic acid; and 3) alternative dehydrating conditions, such as the azeotropic removal of water, and using an acid catalyst and p-toluene sulfinic acid.

Compounds of the formula (II) where p is 2 may also be prepared by reacting, in the presence of a strong base a compound of the formula (VI)—Scheme I, $R_4CH_2NC$ with a compound of the formula (VII)—Scheme I, $ArSO_2L_1$ wherein $R_4$ and Ar are as defined herein and $L_1$ is a leaving group such as halo, e.g. fluoro. Suitable strong bases include, but are not limited to, alkyl lithiums such as butyl lithium or lithium diisopropylamide (Van Leusen et al., *Tetrahedron Letters*, No. 23. 2367–68 (1972)).

The compounds of formula (VI)—Scheme I may be prepared by reacting a compound of the formula (VIII)—Scheme I, $R_4CH_2NH_2$ with an alkyl formate (e.g. ethylformate) to yield an intermediate amide which can be converted to the desired isonitrile by reacting with well known dehydrating agent, such as but not limited to oxalyl chloride, phosphorus oxychloride or tosyl chloride in the presence of a suitable base such as triethylamine.

Alternatively a compound of the formula (VIII)—Scheme I may be converted to a compound of the formula (VI)—Scheme I by reaction with chloroform and sodium hydroxide in aqueous dichloromethane under phase transfer catalysis.

The compounds of the formula (III)—Scheme I may be prepared by reacting a compound of the formula $R_1CHO$ with a primary amine $R_2NH_2$.

The amino compounds of the formula (VIII)—Scheme I are known or can be prepared from the corresponding alcohols, oximes or amides using standard functional group interconversions.

The amino compounds used to prepare the imines of formula (III)—Scheme I are known or can be prepared using standard functional group interconversions (Scheme XII). A particularly useful and general method to prepare these amines is from the a amino acids, which are readily available or if not can be prepared from the corresponding aldehyde using standard amino acid synthesis, such as the Strecker synthesis. The free amino acids or the corresponding amino protected compounds (CBZ, FMOC, or t-BOC) many of which are commercially available can be reduced to the carbinol under standard conditions. For example, borane on the carboxylic acid or if the ester, hydride agents may be employed in the reduction. The protected amino alcohols may be used as intermediates to further elaborate the side chain. Furthermore, protecting groups may be used to mask reactive functionality and thereby facilitate the In formation of the imine and subsequent cycloaddition reaction to form the imidazole. An example of this is the use of a silyl protecting group on a alcohol.

Scheme XII

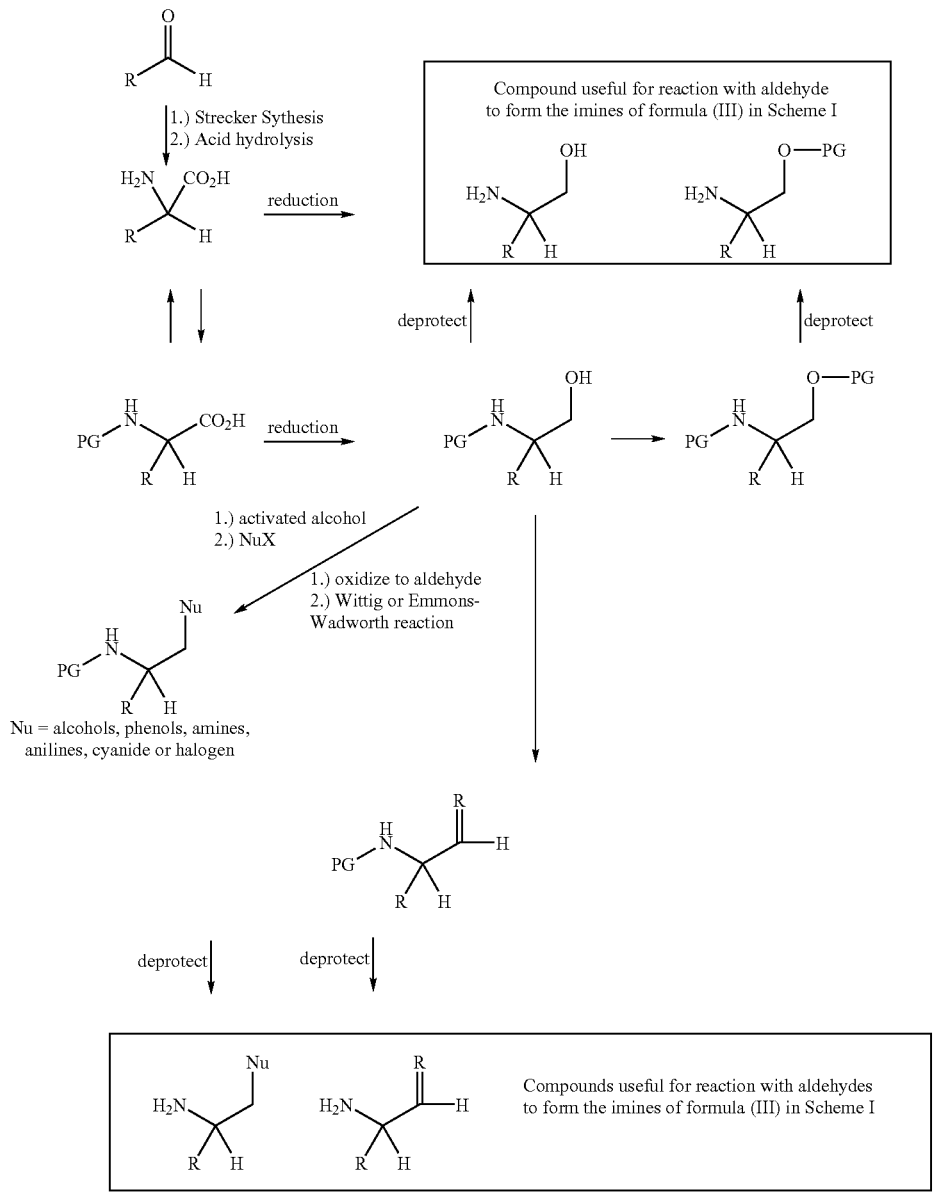

Suitable protecting groups for use with hydroxyl groups and the imidazole nitrogen are well known in the art and described in many references, for instance, Protecting Groups in Organic Synthesis, Greene T W, Wiley-Interscience, New York, 1981. Suitable examples of hydroxyl protecting groups include silyl ethers, such as t-butyldimethyl or t-butyldiphenyl, and alkyl ethers, such as methyl connected by an alkyl chain of variable link, $(CR_{10}R_{20})_n$. Suitable examples of imidazole nitrogen protecting groups include tetrahydropyranyl.

Pharmaceutically acid addition salts of compounds of Formula (I) may be obtained in known manner, for example by treatment thereof with an appropriate amount of acid in the presence of a suitable solvent.

Methods of Treatment

The compounds of Formula (I) or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cell, such as but not limited to monocytes and/or macrophages.

Compounds of Formula (I) are capable of inhibiting proinflammatory cytokines, such as IL-1, IL-6, IL-8, and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine-mediated disease which comprises administering an effective cytokine-interfering amount of a compound of Formula (I) or a pharmaceutically acceptable salt thereof.

Compounds of Formula (I) are capable of inhibiting inducible proinflammatory proteins, such as COX-2, also referred to by many other names such as prostaglandin endoperoxide synthase-2 (PGHS-2) and are therefore of use in therapy. These proinflammatory lipid mediators of the cyclooxygenase (CO) pathway are produced by the inducible COX-2 enzyme. Regulation, therefore of COX-2 which is responsible for the these products derived from arachidonic acid, such as prostaglandins affect a wide variety of cells and tissues are important and critical inflammatory mediators of a wide variety of disease states and conditions. Expression of COX-1 is not effected by compounds of Formula (I). This selective inhibition of COX-2 may alleviate or spare ulcerogenic liability associated with inhibition of COX-1 thereby inhibiting prostoglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management therefore includes treatment of neuromuscular pain, headache, cancer pain, and arthritis pain. Compounds of Formula (I) or a pharmaceutically acceptable salt thereof, are of use in the prophylaxis or therapy in a human, or other mammal, by inhibition of the synthesis of the COX-2 enzyme.

Accordingly, the present invention provides a method of inhibiting the synthesis of COX-2 which comprises administering an effective amount of a compound of Formula (I) or a pharmaceutically acceptable salt thereof. The present invention also provides for a method of prophylaxis treatment in a human, or other mammal, by inhibition of the synthesis of the COX-2 enzyme.

In particular, compounds of Formula (I) or a pharmaceutically acceptable salt thereof are of use in the prophylaxis or therapy of any disease state in a human, or other mammal, which is exacerbated by or caused by excessive or unregulated IL-1, IL-6, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a compound of Formula (I) or a pharmaceutically acceptable salt thereof.

There are many disease states in which excessive or unregulated IL-1 production is implicated in exacerbating and/or causing the disease. These include rheumatoid arthritis, osteoarthritis, stroke, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic β cells disease, and Alzheimer's disease.

In a further aspect, this invention relates to a method of inhibiting the production of TNF in a mammal in need thereof which comprises administering to said mammal an effective amount of a compound of Formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, stroke, cerebral malaria, chronic pulmonary inflammatory disease, silicosis, pulmonary sarcoisosis, bone resorption diseases, such as osteoporosis, reperfusion injury, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis and pyresis.

Compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of Formula (1). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal afflicted with a human immunodeficiency virus (HIV) which comprises administering to such mammal an effective TNF inhibiting amount of a compound of Formula (I) or a pharmaceutically acceptable salt thereof.

Compounds of Formula (I) may also be used in association with the veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The compounds of Formula (I) may also be used topically in the treatment or prophylaxis of topical disease states mediated by or exacerbated by excessive cytokine production, such as by IL-1 or TNF respectively, such as inflamed joints, eczema, psoriasis and other inflammatory skin conditions such as sunburn; inflammatory eye conditions including conjunctivitis; pyresis, pain and other conditions associated with inflammation.

Compounds of Formula (I) have also been shown to inhibit the production of IL-8 (Interleukin-8, NAP). Accordingly, in a further aspect, this invention relates to a method of inhibiting the production of IL-8 in a mammal in need thereof which comprises administering to said mammal an effective amount of a compound of Formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to, a direct reduction in the neutrophil infiltration.

The compounds of Formula (I) are administered in an amount sufficient to inhibit cytokine, in particular IL-1, IL-6, IL-8 or TNF, production such that it is regulated down to normal levels, or in some case to subnormal levels, so as to ameliorate or prevent the disease state. Abnormal levels of IL-1, IL-6, IL-8 or TNF, for instance in the context of the present invention, constitute: (i) levels of free (not cell bound) IL-1, IL-6, IL-8 or TNF greater than or equal to 1 picogram per ml; (ii) any cell associated IL-1, IL-6, IL-8 or TNF; or (iii) the presence of IL-1, IL-6, IL-8 or TNF mRNA above basal levels in cells or tissues in which IL-1, IL-6, IL-8 or TNF, respectively, is produced.

The discovery that the compounds of Formula (I) are inhibitors of cytokines, specifically IL-1, IL-6, IL-8 and TNF is based upon the effects of the compounds of Formulas (I) on the production of the IL-1, IL-8 and TNF in in vitro assays which are described herein.

As used herein, the term "inhibiting the production of IL-1 (IL-6, IL-8 or TNF)" refers to:

a) a decrease of excessive in vivo levels of the cytokine (IL-1, IL-6, IL-8 or TNF) in a human to normal or sub-normal levels by inhibition of the in vivo release of the cytokine by all cells, including but not limited to monocytes or macrophages;

b) a down regulation, at the genomic level, of excessive in vivo levels of the cytokine (IL-1, IL-6, IL-8 or TNF) in a human to normal or sub-normal levels;

c) a down regulation, by inhibition of the direct synthesis of the cytokine (IL-1, IL-6, IL-8 or TNF) as a postranslational event; or d) a down regulation, at the translational level, of excessive in vivo levels of the cytokine (IL-1, IL-6, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-a) and Tumor Necrosis Factor beta (TNF-β).

As used herein, the term "cytokine interfering" or "cytokine suppressive amount" refers to an effective amount of a compound of Formula (I) which will cause a decrease in the in vivo levels of the cytokine to normal or sub-normal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in (a) the initiation and/or maintenance of T cell activation and/or activated T cell-mediated HIV gene expression and/or replication and/or (b) any cytokine-mediated disease associated problem such as cachexia or muscle degeneration.

As TNF-β (also known as lymphotoxin) has close structural homology with TNF-a (also known as cachectin) and since each induces similar biologic responses and binds to the same cellular receptor, both TNF-a and TNF-β are inhibited by the compounds of the present invention and thus are herein referred to collectively as "TNF" unless specifically delineated otherwise.

A new member of the MAP kinase family, alternatively termed CSBP, p38, or RK, has been identified independently by several laboratories. Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the present invention, compounds of Formula (I) have been determined to be potent and selective inhibitors of CSBP/p38/RK kinase activity. These inhibitors are of aid in determining the signaling pathways involvement in inflammatory responses. In particular, for the first time a definitive signal transduction pathway can be prescribed to the action of lipopolysaccharide in cytokine production in macrophages. In addition to those diseases already noted, treatment of stroke, neurotrauma, cardiac and renal reperfusion injury, congestive heart failure, chronic renal failure, angiogenesis & related processes, such as cancer, thrombosis, glomerulonephritis, diabetes and pancreatic b cells, multiple sclerosis, muscle degeneration, eczema, psoriasis, sunburn, and conjunctivitis are also included.

The CSBP inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in the collagen-induced arthritis model and inhibition of TNF production in the endotoxic shock model. In the latter study, the reduction in plasma level of TNF correlated with survival and protection from endotoxic shock related mortality. Also of great importance are the compounds effectiveness in inhibiting bone resorption in a rat fetal long bone organ culture system. Griswold et al., (1988) *Arthritis Rheum.* 31:,1406–1412; Badger, et al., (1989) *Circ. Shock* 27, 51–61; Votta et al., (1994) in vitro. *Bone* 15, 533–538; Lee et al., (1993). B *Ann. N. Y. Acad. Sci.* 696, 149–170.

Chronic diseases which have an inappropriate angiogenic component are various ocular neovasularizations, such as diabetic retinopathy and macular degeneration. Other chronic diseases which have an excessive or increased proliferation of vasculature are tumor growth and metastasis, atherosclerosis, and certain arthritic conditions. Therefore CSBP kinase inhibitors will be of utility in the blocking of the angiogenic component of these disease states.

The term "excessive or increased proliferation of vasculature inappropriate angiogenesis" as used herein includes, but is not limited to, diseases which are characterized by hemangiomas and ocular diseases.

The term "inappropriate angiogenesis" as used herein includes, but is not limited to, diseases which are characterized by vesicle proliferation with accompanying tissue proliferation, such as occurs in cancer, metastasis, arthritis and atherosclerosis.

Accordingly, the present invention provides a method of treating a CSBP kinase mediated disease in a mammal in need thereof, preferably a human, which comprises administering to said mammal, an effective amount of a compound of Formula (I) or a pharmaceutically acceptable salt thereof.

It has now been found that the branching of the $R_2$ moiety, such as in the $R_{22}$ term provides for improved activity against the CSBP enzyme, and for improved in vivo activity versus the unbranced $R_2$ alkyl chain, such as disclosed in U.S. Pat. No. 5,593,992.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid/carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the fFormulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid Formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily, solution include glycerol, diluted alcohol and propylene glycol.

Compounds of Formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular-patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The novel compounds of Formula (I) may also be used in association with the veterinary treatment of mammals, other than humans, in need of inhibition of CSBP/p38 or cytokine inhibition or production. In particular, CSBP/p38 mediated diseases for treatment, therapeutically or prophylactically, in animals include disease states such as those noted herein in the Methods of Treatment section, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The invention will now be described by reference to the following biological examples which are merely illustrative and are not to be construed as a limitation of the scope of the present invention.

BIOLOGICAL EXAMPLES

The cytokine-inhibiting effects of compounds of the present invention may be determined by the following in vitro assays:

Assays for Interleukin-1 (IL-1), Interleukin-8 (IL-8), and Tumour Necrosis Factor (TNF) are well known in the art, and may be found in a number of publications and patents. Representative suitable assays for use herein are described in Adams et al., U.S. Pat. No. 5,593,992, whose disclosure is incorporated by reference in its entirety.

In vivo TNF Assay:
(1) Griswold et al., *Drugs Under Exp. and Clinical Res., XIX* (6), 243–248 (1993); or
(2) Boehm, et al., *Journal Of Medicinal Chemistry* 39, 3929–3937 (1996) whose disclosures are incorporated by reference herein in their entirety.

LPS-induced TNFα Production in Mice and Rats

In order to evaluate in vivo inhibition of LPS-induced TNFα production in rodents, both mice and rats are injected with LPS.

Mouse Method

Male Balb/c mice from Charles River Laboratories are pretreated (30 minutes) with compound or vehicle. After the 30 min. pretreat time, the mice are given LPS (lipopolysaccharide from *Esherichia coli* Serotype 055-85, Sigma Chemical Co., St Louis, Mo.) 25 ug/mouse in 25 ul phosphate buffered saline (pH 7.0) intraperitoneally. Two hours later the mice are killed by $CO_2$ inhalation and blood samples are collected by exsanguination into heparinized blood collection tubes and stored on ice. The blood samples are centrifuged and the plasma collected and stored at −20° C. until assayed for TNFα by ELISA.

Rat Method

Male Lewis rats from Charles River Laboratories are pretreated at various times with compound or vehicle. After a determined pretreat time, the rats are given LPS (lipopolysaccharide from *Esherichia coli* Serotype 055-85, Sigma Chemical Co., St Louis, Mo.) 3.0 mg/kg intraperitoneally. The rats are killed by $CO_2$ inhalation and heparinized whole blood is collected from each rat by cardiac puncture 90 minutes after the LPS injection. The blood samples are centrifuged and the plasma collected for analysis by ELISA for TNFα levels.

ELISA Method

TNFα levels were measured using a sandwich ELISA, as described in Olivera et al., Circ. Shock, 37, 301–306, (1992), whose disclosure is incorporated by reference in its entirety herein, using a hamster monoclonal antimurine TNFα (Genzyme, Boston, Mass.) as the capture antibody and a polyclonal rabbit antimurine TNFa (Genzyme) as the second antibody. For detection, a peroxidase-conjugated goat anti-rabbit antibody (Pierce, Rockford, Ill.) was added, followed by a substrate for peroxidase (1 mg/ml orthophenylenediamine with 1% urea peroxide). TNFα levels in the plasma samples from each animal were calculated from a standard curve generated with recombinant murine TNFα (Genzyme).

LPS-Stimulated Cytokine Production in Human Whole Blood

Assay: Test compound concentrations were prepared at 10× concentrations and LPS prepared at 1 ug/ml (final conc. of 50 ng/ml LPS) and added in 50 uL volumes to 1.5 mL eppendorf tubes. Heparinized human whole blood was obtained from healthy volunteers and was dispensed into eppendorf tubes containing compounds and LPS in 0.4 mL volumes and the tubes incubated at 37 C. Following a 4 hour incubation, the tubes were centrifuged at 5000 rpm for 5 minutes in a TOMY microfuge, plasma was withdrawn and frozen at −80 C.

Cytokine measurement: IL-I and/or TNF were quantified using a standardized ELISA technology. An in-house ELISA kit was used to detect human IL-1 and TNF. Concentrations of IL-1 or TNF were determined from standard curves of the appropriate cytokine and IC50 values for test compound (concentration that inhibited 50% of LPS-stimulated cytokine production) were calculated by linear regression analysis.

CSBP/p38 Kinase Assay:

This assay measures the CSBP/p38-catalyzed transfer of $^{32}$P from [a-$^{32}$P]ATP to threonine residue in an epidermal growth factor receptor (EGFR)-derived peptide (T669) with the following sequence: KRELVEPLTPSGEAPNQALLR (residues 661–681). (See Gallagher et al., "Regulation of Stress Induced Cytokine Production by Pyridinyl Imidazoles: Inhibition of CSBP Kinase", BioOrganic & Medicinal Chemistry, 1997, 5, 49–64).

Reactions were carried in round bottom 96 well plate (from Corning) in a 30 ml volume. Reactions contained (in final concentration): 25 mM Hepes, pH7.5; 8 mM $MgCl_2$; 0.17 mM ATP (the $Km_{[ATP]}$ of p38 (see Lee et al., Nature 300, n72 pg 639–746 (December 1994)); 2.5 uCi of [g-32P] ATP; 0.2 mM sodium orthovanadate; 1 mM DTT; 0.1% BSA; 10% glycerol; 0.67 mM T669 peptide; and 2–4 nM of yeast-expressed, activated and purified p38. Reactions were initiated by the addition of [gamma-32P]Mg/ATP, and incubated for 25 min. at 37° C. Inhibitors (dissolved in DMSO) were incubated with the reaction mixture on ice for 30 minutes prior to adding the $^{32}$P-ATP. Final DMSO concentration was 0.16%. Reactions were terminated by adding 10 ul of 0.3 M phosphoric acid, and phosphorylated peptide was isolated from the reactions by capturing it on p81 phosphocellulose filters. Filters were washed with 75 mM phosphoric acids, and incorporated 32P was quantified using beta scintillation counter. Under these conditions, the specific activity of p38 was 400–450 pmol/pmol enzyme, and the activity was linear for up to 2 hr of incubation. The kinase activity values were obtained after subtracting values generated in the absence of substrate which were 10–15% of total values.

Representative final compounds of Formula (I), Examples 1 to 23 have demonstrated positive inhibitory activity of an $IC_{50}$ of <50 uM in this binding assay or a similar assay.

Prostoglandin Endoperoxide Synthase-2 (PGHS-2) Assay:

This assay describes a method for determining the inhibitory effects of compounds of Formula (I) on human PGHS-2 protein expression in LPS stimulated human monocytes. A suitable assay for PGHS-2 protein expression may be found in a number of publications, including U.S. Pat. No. 5,593,992 whose disclosure is incorporated herein by reference.

TNF-a in Traumatic Brain Injury Assay

This assay provides for examination of the expression of tumor necrosis factor mRNA in specific brain regions which follow experimentally induced lateral fluid-percussion traumatic brain injury (TBI) in rats. Since TNF-a is able to induce nerve growth factor (NGF) and stimulate the release of other cytokines from activated astrocytes, this post-traumatic alteration in gene expression of TNF-a plays an important role in both the acute and regenerative response to CNS trauma. A suitable assay may be found in WO 97/35856 whose disclosure is incorporated herein by reference.

CNS Injury Model for IL-b mRNA

This assay characterizes the regional expression of interleukin-1β (IL-1β) mRNA in specific brain regions following experimental lateral fluid-percussion traumatic brain injury (TBI) in rats. Results from these assays indicate that following TBI, the temporal expression of IL-1β mRNA is regionally stimulated in specific brain regions. These regional changes in cytokines, such as IL-1β play a role in the post-traumatic pathologic or regenerative sequelae of brain injury. A suitable assay may be found in WO 97/35856 whose disclosure is incorporated herein by reference.

Angiogenesis Assay:

Described in WO 97/32583, whose disclosure is incorporated herein by reference, is an assay for determination of inflammatory angiogenesis which may be used to show that cytokine inhibition will stop the tissue destruction of excessive or inappropriate proliferation of blood vessels.

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions run under anhydrous conditions in an argon atmosphere unless otherwise indicated.

In the Examples, all temperatures are in degrees Centigrade (° C.). Mass spectra were performed upon a VG Zab mass spectrometer using fast atom bombardment or on a micromass platform electrospray ionization mass spectrometer in the positive ion mode using 95:5 $CH_3CN/CH_3OH$ with 1% formic acid as the carrier solvent, unless otherwise indicated. $^1$H-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant.

Flash chromatography is run over Merck Silica gel 60 (230–400 mesh).

Example 1

(S)-1-(1-Hydroxyprop-2-yl)-4-(4-fluorophenyl)-5-[2-(4-fluorophenoxy)pyrimidin-4-yl]imidazole a) 4-Fluorophenyl-tolylsulfonomethylformamide To a suspension of p-toluenesulfinic acid sodium salt (30 grams, hereinafter "g") in $H_2O$ (100 milliliters (hereinafter "mL")) was added methyl t-butyl ether (50 mL) followed by dropwise addition of conc. HCl (15 mL). After stirring 5 min., the organic phase was removed and the aqueous phase was extracted with methyl t-butyl ether. The organic phase was dried ($Na_2SO_4$) and concentrated to near dryness. Hexane was added and the free acid was filtered. The p-toluenesulfinic acid (22 g, 140.6 millimole (hereinafter "mmol")), p-fluorobenzaldehyde (22 mL, 206 mmol), formamide (20 mL, 503 mmol) and camphor sulphonic acid (4 g, 17.3 mmol) were combined and stirred at 60° C. for about 18 hours (hereinafter "h"). The resulting solid was broken up and stirred with a mixture of MeOH (35 mL) and hexane (82 mL) then filtered. The solid was resuspended in MeOH/hexane (1:3, 200 mL) and stirred vigorously to break up remaining chunks. Filtration afforded the title compound (27 g, 62% yield). $^1$H NMR (400 MHz, $CDCl_3$): d 8.13 (s, 1H), 7.71 (d, 2H), 7.43 (dd, 2H), 7.32 (d, 2H), 7.08 (t, 2H), 6.34 (d, 1H), 2.45 (s, 3H).

b) 4-Fluorophenyl-tolylsulfonomethylisocyanide

The compound in the previous step (2.01 g, 6.25 mmol) in ethyleneglycol dimethylether (DME) (32 mL) was cooled to −10° C. POCl₃ (1.52 mL, 16.3 mmol) was added followed by the dropwise addition of triethylamine (4.6 mL, 32.6 mmol) in DME (3 mL) keeping the internal temperature below −5° C. The mixture was gradually warmed over 1 h., quenched in H₂O and extracted with EtOAc. The organic phase was washed with saturated aqueous NaHCO₃, dried (Na₂SO₄), and concentrated. The resulting residue was triturated with petroleum ether and filtered to afford the title compound (1.7 g, 90% yield). ¹H NMR (CDCl₃): d 7.63 (d, 2H), 7.33 (m, 4H), 7.10 (t, 2H), 5.60 (s, 1H), 2.50 (s, 3H)

c) 2-Propylthiopyrimidine-4-carboxaldehyde dimethyl acetal

Charge a 1 L 3-necked flask equipped with a stir bar, thermometer, 100 mL addition funnel and reflux condensor with N,N-dimethylformamide dimethyl acetal (88.7 g, 98.9 mL, 700 mmol) and pyruvaldehyde dimethyl acetal (85.3 g, 86.8 mL, 700 mmol) and heat in an oil bath at 110° C. for 3–4 h. Cool the solution to 85° C. and add thiourea (48.9 g, 636.4 mmol) and NaOMe (25 wt % in MeOH, 151.2 g, 160 mL, 700 mmol) and stir at 85° C. for 3–4 h. Cool the solution to 65° C. and charge 1-bromoropane (86.9 g, 64.4 mL, 700 mmol) to the addition funnel and add slowly over 10–15 min to the reaction, bringing the solution to a mild reflux. After 1 h, add 100 mL of EtOAC to the reaction and bring the oil bath temperature to 95° C. Replace the reflux condensor with a distillation head and distill 150–200 mL of solvent from the reaction. Add an additional 400 mL of EtOAc and 120 mL of H₂O and stir at 50° C. for 5 min. Transfer to a separatory funnel and separate the aqueous phase. Add 60 mL of H₂O, agitate, and separate the aqueous phase. A sample was concentrated to give a yellow oil: ¹H NMR (300 MHz, CDCl₃) d 8.53 (11H, d, J 5.0 Hz), 7.16(1H, d, J=5.0 Hz), 5.17 (1H, s), 3.42 (3H, s), 3.14 (2H, t, J=7.3 Hz), 1.76 (2H, m), 1.05 (3H, t, J=7.3 Hz).

Alternatively, bromopropane can be replaced with any suitable alkyl halide and the alkylation process can occur at about 0 to about 100° C.

d) 2-Propylthiopyrimidine-4-carboxaldehyde

The product of the previous step (24 g, 105 mmol) was dissolved in THF (75 mL) and 3N HCL (150 mL) was added. The resulting mixture was stirred under argon and heated to 57° C. for 4 h. The THF was stripped off and the mixture was cooled in an ice bath. EtOAc (300 mL) was added followed by the addition of solid NaHCO₃. Additional H₂O was added to dissolve all the solid, and the aqueous phase was extracted with EtOAc (3×150 mL). The organic phases were combined, dried (Na₂SO₄) and concentrated to give a brown oil. The crude product was purified by flash chromatography (silica gel, 0–1% MeOH/CH₂Cl₂) to give the title compound as a yellow oil. ¹H NMR (400 MHz, CDCl₃): d 9.95 (s, 1H), 8.78 (d, 1H), 7.45 (d, 1H), 3.21 (t, 2H), 1.82 (m, 2H), 1.1 (t, 3H).

e) 2-Propylthiopyrimidine-4-carboxaldehyde[(S)-2-amino-1-propanol]imine

To a solution of 2-propylthiopyrimidine-4-carboxaldehyde (10.9 g, 60 mmol) in CH₂Cl₂ (200 mL) was added (S)-2 amino-1-propanol (5.85 g, 78 mmol). The solution was stirred at room temperature under argon for 16 h. The solution was concentrated to give the title compound. ES (+) MS m/e=240 (MH⁺)

f) (S)-1-(1-Hydroxyprop-2-yl)-4-(4-fluorophenyl)-5-[2-(propylthio)pyrrimidin-4-yl]imidazole The product of the previous step (14.7 g, ~60 mmol) was dissolved in DMF (200 mL) and stirred under argon. Potassium carbonate (6.6, g, 48 mmol) was added followed by the addition of the product of example 1(b) (12.14 g, 42 mmol). The mixture was stirred at rt for 72 h. The DMF was pumped off and the residue was partitioned between EtOAc and water. The organic phase was separated, washed with brine, dried (Na₂SO₄), and concentrated. The crude product was purified by flash chromatography (silica gel, 0–4% MeOH/CH₂Cl₂) to give the title compound as a yellow solid. ES (+) MS m/e=373 (MH⁺)

g) (S)-1-(1-Hydroxyprop-2-yl)-4-(4-fluorophenyl)-5-[2-(propylsulfonyl)pyrimidin-4-yl]imidazole The product of example 1(f) (4 g, 10.75 mmol) was dissolved in methanol (100 mL) and cooled in an ice bath while stirring under argon. OXONE (8.26 g, 13.44) mmol in H₂O (60 mL) was added and the mixture was stirred at rt for 12 h. The MeOH was stripped and the residue partitioned between EtOAc and H₂O. The mixture was made basic by the addition of solid K2CO₃ and extracted with EtOAc. the combined organic extracts were washed with brine, dried (Na₂SO₄), and concentrated to give the title compound as a yellow solid. ES (+) MS m/e=405 (MH⁺)

h) (S)-1-(1-Hydroxyprop-2-yl)-4-(4-fluorophenyl)-5-[2-(4-fluorophenoxy)-pyrimidin-4-yl]imidazole NaH (95%) (252 mg, 10 mmol) was added in small portions to absolution of 4-fluorophenol (2.21 g, 19.8 mmol) in dry THF (50 mL). After the vigorous reaction had subsided, this solution was added to a solution of the product of example 1 (g) (2 g, 4.95 mmol) dissolved in dry THF (200 mL). The reaction mixture was stirred at rt under argon for 1 h. The reaction mixture was concentrated, and the residue partitioned between EtOAc and H₂O. The organic phase was washed with 1N NaOH, brine, dried (Na₂SO₄), and concentrated. The crude product was purified by flash chromatography (silica gel, 0–4% MeOH/CH₂Cl₂) to give the title compound as a light yellow solid. ES (+) MS m/e=409 (MH⁺)

Example 2

(R)-1-(1-Hydroxyprop-2-yl)-4-(4-fluorophenyl)-5-[2-(4-fluorophenoxy)pyrimidin-4-yl]imidazole Following the procedures of examples 1 (e)–(h) except using (R)-2 amino-1-propanol in place of (S)-2 amino-1-propanol in step 1 (e) afforded the title compound as an off-white solid. ES (+) MS m/e=409 (MH⁺)

Example 3

1-(1,3-Dihydroxyprop-2-yl)-4-(4-fluorophenyl)-5-[2-(4-fluorophenoxy)pyrimidin-4-yl]imidazole Following the procedures of examples 1 (e)–(h) except using 2-amino-1,3-propanediol in place of (S)-2-amino-1-propanol in step 1 (e) afforded the title compound as an off-white solid. ES (+) MS m/e=425 (MH⁺)

Example 4

(R)-1-(1-Hydroxyprop-2-yl)-4-(4-fluorophenyl)-5-(2-phenoxypyrimidin-4-yl)imidazole Following the procedures of examples 1 (e)–(h) except using (R)-2 amino-1-propanol in place of (S)-2 amino-1-propanol in step 1 (e) and using phenol in place of 4-fluorophenol in step 1 (h) afforded the title compound as light yellow crystals. ES (+) MS m/e=391 (MH+)

Example 5

(S)-1-(-Hydroxyprop-2-yl)-4-(4-fluorophenyl)-5-(2-phenoxypyrimidin-4-yl)imidazole Following the procedure of example 1 (h) except using phenol in place of 4-fluorophenol, afforded the title compound as light yellow crystals. ES (+) MS m/e=391 (MH+)

Example 6

(+/−)-1-(1-Hydroxyprop-2-yl)-4-(4-fluorophenyl)-5-(2-phenoxypyrimidin-4-yl)imidazole Following the procedures of examples 1(e)–(h) except using (+/−)-2 amino-1-propanol in place of (S)-2 amino-1-propanol in step 1 (e) and using phenol in place of 4-fluorophenol in step 1 (h) afforded the title compound as light yellow crystals. ES (+) MS m/e=391 (MH+)

Example 7

(+/−)-1-(1-Phenoxyprop-2-yl)$_4$-(4-fluorophenyl)-5-(2-phenoxypyrimidin-4-yl)imidazole Following the procedures of examples 1 (e)–(h) except using (+/−)-1-phenoxy-2-aminopropane in place of (S)-2 amino-1-propanol in step 1 (e) and using phenol in place of 4-fluorophenol in step 1 (h) afforded the title compound as a light yellow solid. ES (+) MS m/e=467 (MH+)

Example 8

(R)-1-(1-Hydroxy-3-phenylprop-2-yl)-4-(4-fluorophenyl)-5-(2-phenoxypyrimidin-4-yl)imidazole Following the procedures of examples 1 (e)–(h) except using (R)-2 amino-3-phenyl-1-propanol in place of (S)-2 amino-1-propanol in step 1 (e) and using phenol in place of 4-fluorophenol in step 1 (h) afforded the title compound as yellow solid. ES (+) MS m/e=467 (MH+)

Example 9

(S)-1-(1-Hydroxy-3-phenylprop-2-yl)-4-(4-fluorophenyl)-5-(2-phenoxypyrimidin-4-yl)imidazole Following the procedures of examples 1 (e)–(h) except using (S)-2 amino-3-phenyl-1-propanol in place of (S)-2 amino-1-propanol in step 1 (e) and using phenol in place of 4-fluorophenol in step 1 (h) afforded the title compound as a yellow solid. ES (+) MS m/e=467 (MH+)

Example 10

(R)-1-(1-Hydroxybut-2-yl)-4-(4-fluorophenyl)-5-(2-phenoxypyrimidin-4-yl)imidazole Following the procedures of examples 1 (e)–(h) except using (R)-2 amino-1-butanol in place of (S)-2 amino-1-propanol in step 1 (e) and using phenol in place of 4-fluorophenol in step 1 (h) afforded the title compound as white solid. ES (+) MS m/e=405 (MH+)

Example 11

(S)-1-(1-Hydroxybut-2-yl)-4-(4-fluorophenyl)-5-(2-phenoxypyrimidin-4-yl)imidazole Following the procedures of examples 1 (e)–(h) except using (S)-2 amino-1-butanol in place of (S)-2 amino-1-propanol in step 1 (e) and using phenol in place of 4-fluorophenol in step 1 (h) afforded the title compound as white solid. ES (+) MS m/e=405 (MH+)

Example 12

1-(1,3-Dihydroxyprop-2-yl)-4-(4-fluorophenyl)-5-(2-phenoxypyrimidin-4-yl)imidazole Following the procedures of examples 1 (e)–(h) except using 2-amino-1,3-propanediol in place of (S)-2 amino-1-propanol in step 1 (e) and using phenol in place of 4-fluorophenol in step 1 (h) afforded the title compound as a white solid. ES (+) MS m/e=407 (MH+)

Example 13

(R)-1-(1-Hydroxy-2-phenyleth-2-yl)$_4$-(4-fluorophenyl)-5-(2-phenoxypyrimidin-4-yl)imidazole Following the procedures of examples 1 (e)–(h) except using (R)-2-amino-2-phenylethanol in place of (S)-2 amino-1-propanol in step 1 (e) and using phenol in place of 4-fluorophenol in step 1 (h) afforded the title compound as a white solid. ES (+) MS m/e=453 (MH+)

Example-14

(S)-1-(1-Hydroxy-2-phenyleth-2-yl)-4-(4-fluorophenyl)-5-(2-phenoxypyrimidin-4-yl)imidazole Following the procedures of examples 1 (e)–(h) except using (S)-2-amino-2-phenylethanol in place of (S)-2 amino-1-propanol in step 1 (e) and using phenol in place of 4-fluorophenol in step 1 (h) afforded the title compound as a white solid. ES (+) MS m/e=453 (MH+)

Example-15

(S)-1-(1-Hydroxyprop-2-yl)-4-(4-fluorophenyl)-5-[2-(4-chlorophenoxy)pyrimidin-4-yl]imidazole Following the procedure of example 1 (h) except using 4-chlorophenol in place of 4-fluorophenol, afforded the title compound as a white solid. ES (+) MS m/e=425 (MH+)

Example 16

(R)-1-(1-Hydroxybut-2-yl)-4-(4-fluorophenyl)-5-[2-(4-chlorophenoxy)pyrimidin-4-yl]imidazole Following the procedures of examples 1 (e)–(h) except using (R)-2 amino-1-butanol in place of (S)-2 amino-1-propanol in step 1 (e) and using 4-chlorophenol in place of 4-fluorophenol in step 1 (h) afforded the title compound as a white solid. ES (+) ES (+) MS m/e=439 (MH+)

Example 17

(S)-1-(1-Hydroxybut-2-yl)$_4$-(4-fluorophenyl)-5-[2-(4-chlorophenoxy)pyrimidin-4-yl]imidazole Following the procedures of examples 1 (e)–(h) except using (S)-2 amino-1-butanol in place of (S)-2 amino-1-propanol in step 1 (e) and using 4-chlorophenol in place of 4-fluorophenol in step 1 (h) afforded the title compound as white solid. ES (+) MS n/e=439 (MH$^+$)

Example 18

(S)-1-(1-Hydroxyprop-2-yl)-4-(4-fluorophenyl)-5-[2-(4-methylphenoxy)pyrimidin-4-yl]imidazole Following the procedure of example 1 (h) except using 4-methylphenol in place of 4-fluorophenol, afforded the title compound as a white solid. ES (+) MS m/e=405 (MH$^+$)

Example 19

(R)-1-(1-Hydroxybut-2-yl)$_4$-(4-fluorophenyl)-5-[2-(4-methylphenoxy)pyrimidin-4-yl]imidazole Following the procedures of examples 1 (e)–(h) except using (R)-2 amino-1-butanol in place of (S)-2 amino-1-propanol in step 1 (e) and using 4-methylphenol in place of 4-fluorophenol in step 1 (h) afforded the title compound as white solid. ES (+) MS m/e=419 (MH$^+$)

Example 20

(S)-1-(1-Hydroxybut-2-yl)-4-(4-fluorophenyl)-5-[2-(4-methylphenoxy)pyrimidin-4-yl]imidazole Following the procedures of examples 1 (e)–(h) except using (S)-2 amino-1-butanol in place of (S)-2 amino-1-propanol in step 1 (e) and using 4-methylphenol in place of 4-fluorophenol in step 1 (h) afforded the title compound as white solid. ES (+) MS n/e=419 (MH$^+$)

Example 21

1-(1,3-Dihydroxyprop-2-yl)-4-(4-fluorophenyl)-5-[2-(4-methylphenoxy)pyrimidin-4-yl]imidazole Following the procedures of examples 1 (e)–(h) except using 2-amino-1,3-propanediol in place of (S)-2 amino-1-propanol in step 1 (e) and using 4-methylphenol in place of 4-fluorophenol in step 1 (h) afforded the title compound as a white solid. ES (+) MS m/e=421 (MH$^+$)

Example 22

(S)-1-(4-N-Molpholinyl-2-but-yl)-4-(4-fluorophenyl)-5-(2-phenoxypyrimidiny-4-yl)imidazole a) (S)-3-(t-butoxycarbonylamino)-1-butanol Methyl (S)-3-(t-butoxycarbonylamino)-1-butyrate prepared according to (McIntosh and Acquaah, *Can. J. Chem* 66, 1752 (1988)) (3 g, 13.8 mmol) was dissolved in dry THF (100 mL) and cooled in an ice bath while stirring under argon. Lithium borohydride (305 mg, 13.9 mmol) was added and the mixture allowed to warm to room temperature and stir for 16 hours. The solvent was evaporated and the residue taken up in EtOAc, washed with brine, dried (Na$_2$SO$_4$), and concentrated. The crude product was purified by flash chromatography (silica gel, 0–20% EtOAc/hexane) to give the title compound as a white solid. ES (+) MS m/e=190 (MH$^+$)

b) (S)-3-(t-butoxycarbonylamino)-1-butanol Mesylate

The product of example 22 (a) (1.06 g, 5.6 mmol) was dissolved in CH$_2$Cl$_2$ (10 ml) and cooled in an ice bath while stirring under argon. Triethylamine (0.667 g, 6.6 mmol) was added followed by the dropwise addition of methanesulfonyl chloride (0.687 g, 6 mmol). After 10 minutes the ice bath was removed and the mixture stirred at rt for 2 h. The solvent was stripped off and the title compound was isolated as a yellow oil. ES (+) MS m/e=268 (MH$^+$), 290 (MNa$^+$)

c) 4-[(S)-3-(t-butoxycarbonylamino)but-1-yl]morpholine

The crude product of example 22 (b) (~5.6 mmol) was dissolved in morpholine (10 mL) and heated to 57° C. while stirring under argon for 1 h. The solvent was pumped off, and the residue was partitioned between EtOAc and water. The organic phase was washed with brine, dried (Na$_2$SO$_4$), and concentrated. The crude product was purified by flash chromatography (silica gel, 2–5% MeOH/CH$_2$Cl$_2$) to give the title compound as a white solid. ES (+) MS m/e=259 (MH$^+$)

d) 4-(3-aminobut-1-yl)morpholine

The product of example 22 (c) (0.41 g, 1.59 mmol) was dissolved in CH$_2$Cl$_2$ (10 mL) and cooled in an ice bath while stirring under argon. A solution of trifluoroacetic acid (5 mL) in CH$_2$Cl$_2$ (5 mL) was added and the mixture allowed to warm to room temperature for 1 h. The solvents were evaporated to give the title compound as an oil. ES (+) MS m/e=159 (MH$^+$)

e) (S)-1-(4-N-Morpholinyl-2-but-yl)-4-(4-fluorophenyl)-5-(2-phenoxypyrimidiny-4-yl)imidazole Following the procedures of examples 1 (e)–(h) except using the crude product of 22 (d) plus excess triethylamine in place of (S)-2 amino-1-propanol in step 1 (e) and using phenol in place of 4-fluorophenol in step 1 (h) afforded the title compound as a pink solid ES (+) MS m/e=474 (MH$^+$)

By analagous methods to those indicated above the following compounds may be prepared:

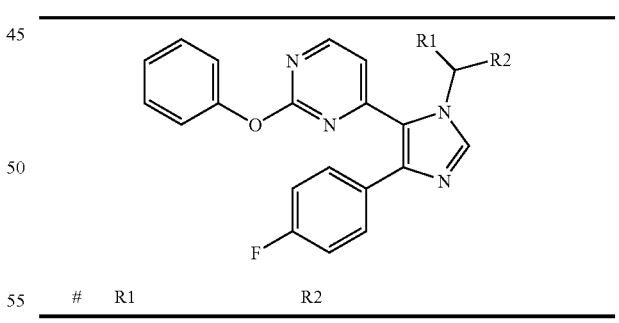

| # | R1 | R2 |
|---|---|---|
| 23 | methyl | hydroxymethyl |
| 24 | ethyl | hydroxymethyl |
| 25 | isopropyl | hydroxymethyl |
| 26 | 2-(methyl)propyl | hydroxymethyl |
| 27 | phenyl | hydroxymethyl |
| 28 | benzyl | hydroxymethyl |
| 29 | phenethyl | hydroxymethyl |
| 30 | methyl | dimethylaminomethyl |
| 31 | ethyl | dimethylaminomethyl |
| 32 | isopropyl | dimethylaminomethyl |
| 33 | 2-(methyl)propyl | dimethylaminomethyl |
| 34 | phenyl | dimethylaminomethyl |
| 35 | benzyl | dimethylaminomethyl |

-continued

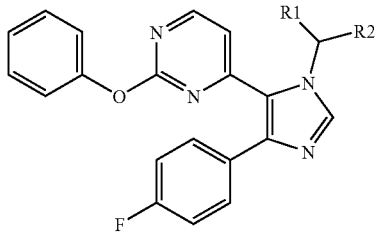

| # | R1 | R2 |
|---|---|---|
| 36 | phenethyl | dimethylaminomethyl |
| 37 | methyl | carboxy |
| 38 | ethyl | carboxy |
| 39 | isopropyl | carboxy |
| 40 | 2-(methyl)propyl | carboxy |
| 41 | phenyl | carboxy |
| 42 | benzyl | carboxy |
| 43 | phenethyl | carboxy |
| 44 | methyl | —CONH$_2$ |
| 45 | methyl | —CONHMe |
| 46 | methyl | —CONMe$_2$ |
| 47 | methyl | methoxymethyl |
| 48 | methyl | phenoxymethyl |
| 49 | methyl | benzyloxymethyl |
| 50 | methyl | carbamoylmethyl |
| 51 | methyl | carbamoylmethyl |
| 52 | methyl | aminomethyl |
| 53 | methyl | N-(methyl)aminomethyl |
| 54 | methyl | N-(dimethyl)aminomethyl |
| 55 | methyl | N-(benzyl)aminomethyl |
| 56 | methyl | aceramidomethyl |
| 57 | methyl | benzamidomethyl |
| 58 | methyl | methanesulfonamidomethyl |
| 59 | methyl | benzenesulfonamidomethyl |
| 60 | methyl | phenylmethylsulfonamidomethyl |
| 61 | methyl | N'-ethylureidomethyl |
| 62 | methyl | N'-phenylureidomethyl |
| 63 | methyl | —CH2OCH2CH2Ph |
| 64 | methyl | —CONHPh |
| 65 | methyl | —CONHBn |
| 66 | methyl | —CH2OCH2(4-MePh) |
| 67 | methyl | —CH2OCH2(4-FPh) |
| 68 | methyl | —CH2OCH2(4-ClPh) |
| 69 | methyl | —CH2OCH2(3-ClPh) |
| 70 | methyl | —CH2O(4-MePh) |
| 71 | methyl | —CH2O(4-FPh) |
| 72 | methyl | —CH2O(4-ClPh) |
| 73 | methyl | —CH2O(3-ClPh) |
| 74 | ethyl | —CONH$_2$ |
| 75 | ethyl | —CONHMe |
| 76 | ethyl | CONMe$_2$ |
| 77 | ethyl | methoxymethyl |
| 78 | ethyl | phenoxymethyl |
| 79 | ethyl | benzyloxymethyl |
| 80 | ethyl | carbamoyl |
| 81 | ethyl | carbamoylmethyl |
| 82 | ethyl | aminomethyl |
| 83 | ethyl | N-(methyl)aminomethyl |
| 84 | ethyl | N-(dimethyl)aminomethyl |
| 85 | ethyl | N-(benzyl)aminomethyl |
| 86 | ethyl | acetamidomethyl |
| 87 | ethyl | benzamidomethyl |
| 88 | ethyl | methanesulfonamidomethyl |
| 89 | ethyl | benzenesulfonamidomethyl |
| 90 | ethyl | phenylmethylsulfonamidomethyl |
| 91 | ethyl | N'-ethylureidomethyl |
| 92 | ethyl | N'-phenlureidomethyl |
| 93 | ethyl | —CH2OCH2CH2Ph |
| 94 | ethyl | —CONHPh |
| 95 | ethyl | —CONHBn |
| 96 | ethyl | —CH2OCH2(4-MePh) |
| 97 | ethyl | —CH2OCH2(4-FPh) |
| 98 | ethyl | —CH2OCH2(4-ClPh) |
| 99 | ethyl | —CH2OCH2(3-ClPh) |

-continued

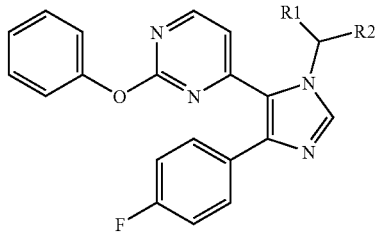

| # | R1 | R2 |
|---|---|---|
| 100 | ethyl | —CH2O(4-MePh) |
| 101 | ethyl | —CH2O(4-FPh) |
| 102 | ethyl | —CH2O(4-ClPh) |
| 103 | ethyl | —CH2O(3-ClPh) |

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

The invention claimed is:
1. A process for preparing a compound of Formula (I)

(I)

wherein
R$_1$ is a pyrimidinyl ring, which ring is substituted with Y—R$_a$ and optionally with an additional independent substituent selected from C$_{1-4}$ alkyl, halogen, hydroxyl, C$_{1-4}$ alkoxy, C$_{1-4}$ alkylthio, C$_{1-4}$ alkylsulfinyl, CH$_2$OR$_{12}$, amino, mono and di-C$_{1-6}$ alkyl substituted amino, an N-heterocyclyl ring which ring has from 5 to 7 members and optionally contains an additional heteroatom selected from oxygen, sulfur or NR$_{15}$, N(R$_{10}$) C(O)R$_b$ or NHR$_a$;

Y is oxygen or sulfur;

R$_4$ is phenyl, naphth-1-yl or naphth-2-yl which is optionally substituted by one or two substituents, each of which is independently selected, and, which, for a 4-phenyl, 4-naphth-1-yl, 5-naphth-2-yl or 6-naphth-2-yl substituent, is halogen, cyano, nitro, C(Z)NR$_7$R$_{17}$, C(Z)OR$_{16}$, (CR$_{10}$R$_{20}$)$_v$COR$_{12}$, SR$_5$, SOR$_5$, OR$_{12}$, halosubstituted-C$_{1-4}$ alkyl, C$_{1-4}$ alkyl, ZC(Z)R$_{12}$, NR$_{10}$C(Z)

R₁₆, or (CR₁₀R₂₀)ᵥNR₁₀R₂₀ and which, for other positions of substitution, is halogen, cyano, C(Z)NR₁₃R₁₄, C(Z)OR₃,(CR₁₀R₂₀)ₘ″COR₃, S(O)ₘR₃, OR₃, halo-substituted-C₁₋₄ alkyl, C₁₋₄ alkyl, (CR₁₀R₂₀)ₘ″NR₁₀C(Z)R₃, NR₁₀S(O)ₘR₈, NR₁₀S(O)ₘNR₇R₁₇, ZC(Z)R₃ or (CR₁₀R₂₀)ₘ″NR₁₃R₁₄;

Z is oxygen or sulfur;
n is an integer having a value of 1 to 10;
m is 0, or the integer 1 or 2;
m′ is an integer having a value of 1 or 2,
m″ is 0, or an integer having a value of 1 to 5;
v is 0, or an integer having a value of 1 or 2;
R₂ is —C(H)(A)(R₂₂);
A is an optionally substituted aryl, heterocyclyl, or heteroaryl ring, or A is a substituted C₁₋₁₀ alkyl;
R₂₂ is a substituted C₁₋₁₀ alkyl;
Rₐ is aryl, aryl C₁₋₆alkyl, heterocyclic, heterocyclyl C₁₋₆ alkyl, heteroaryl, heteroaryl C₁₋₆alkyl, wherein each of these moieties may be optionally substituted;
R_b is hydrogen, C₁₋₆ alkyl, C₃₋₇ cycloalkyl, aryl, arylC₁₋₄ alkyl, heteroaryl, heteroarylC₁₋₄alkyl, heterocyclyl, or heterocyclyl C₁₋₄ alkyl, wherein each of these moieties may be optionally substituted;
R₃ is heterocyclyl, heterocyclylC₁₋₁₀ alkyl or R₈;
R₅ is hydrogen, C₁₋₄ alkyl, C₂₋₄ alkenyl, C₂₋₄ alkynyl or NR₇R₁₇, excluding the moieties SR₅ being SNR₇R₁₇ and SOR₅ being SOH;
R₇ and R₁₇ is each independently selected from hydrogen or C₁₋₄ alkyl or R₇ and R₁₇ together with the nitrogen to which they are attached form a heterocyclic ring of 5 to 7 members which ring optionally contains an additional heteroatom selected from oxygen, sulfur or NR₁₅;
R₈ is C₁₋₁₀ alkyl, halo-substituted C₁₋₁₀ alkyl, C₂₋₁₀ alkenyl, C₂₋₁₀ alkynyl, C₃₋₇ cycloalkyl, C₅₋₇ cycloalkenyl, aryl, aryl C₁₋₁₀ alkyl, heteroaryl, heteroarylC₁₋₁₀ alkyl, (CR₁₀R₂₀)ₙOR₁₁, (CR₁₀R₂₀)ₙS(O)ₘR₁₈, (CR₁₀R₂₀)ₙNHS(O)₂R₁₈, (CR₁₀R₂₀)ₙNR₁₃R₁₄; wherein the aryl, arylalkyl, heteroaryl, heteroaryl alkyl may be optionally substituted;
R₉ is hydrogen, C(Z)R₁₁ or optionally substituted C₁₋₁₀ alkyl, S(O)₂R₁₈, optionally substituted aryl or optionally substituted aryl-C₁₋₄ alkyl;
R₁₀ and R₂₀ is each independently selected from hydrogen or C₁₋₄ alkyl;
R₁₁ is hydrogen, C₁₋₁₀ alkyl, C₃₋₇ cycloalkyl, heterocyclyl, heterocyclyl C₁₋₁₀ alkyl, aryl, arylC₁₋₁₀ alkyl, heteroaryl or heteroarylC₁₋₁₀ alkyl, wherein these moieties may be optionally substituted;
R₁₂ is hydrogen or R₁₆;
R₁₃ and R₁₄ is each independently selected from hydrogen or optionally substituted C₁₋₄ alkyl, optionally substituted aryl or optionally substituted aryl-C₁₋₄ alkyl, or together with the nitrogen which they are attached form a heterocyclic ring of 5 to 7 members which ring optionally contains an additional heteroatom selected from oxygen, sulfur or NR₉;
R₁₅ is R₁₀ or C(Z)—C₁₋₄ alkyl;
R₁₆ is C₁₋₄ alkyl, halo-substituted-C₁₋₄ alkyl, or C₃₋₇ cycloalkyl;
R₁₈ is C₁₋₁₀ alkyl, C₃₋₇ cycloalkyl, heterocyclyl, aryl, aryl₁₋₁₀alkyl, heterocyclyl, heterocyclyl-C₁₋₁₀alkyl, heteroaryl or heteroaryl₁₋₁₀alkyl;
or a pharmaceutically acceptable salt thereof;
which comprises reacting a compound of the Formula (II):

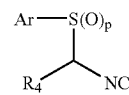

(II)

with a imine compound of the Formula (III):

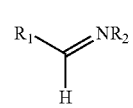

(III)

wherein p is 0 or 2; and a base strong enough to deprotonate the isonitrile moiety of Formula (II); and R₁₁, R₂ and R₄ are as defined in Formula (I), or are precursors of the groups R₁, R₂ and R₄ and Ar is an optionally substituted phenyl group, and thereafter if necessary, converting a precursor of R₁, R₂ and R₄ to a group R₁, R₂ and R₄.

2. The process according to claim 1 wherein p=0.
3. The process according to claim 1 wherein p=2.
4. The process according to claim 3 wherein the base is an amine, a carbonate, a hydride, or an alkyl or aryl lithium reagent.
5. The process according to claim 3 wherein the imine of Formula (III), is isolated prior to reaction with Formula (II).
6. The process according to claim 3 wherein the imine of Formula (III), is formed in situ prior to reaction with Formula (II).
7. The process according to claim 6 wherein the imine is formed in situ by reacting an aldehyde of the formula R₁CHO, wherein R₁ is as defined for Formula (I), with a primary amine of the formula R₂NH₂, wherein R₂ is as defined for Formula (I).
8. The process according to claim 7 wherein formation of the imine in situ utilizes dehydrating conditions.
9. The process according to claim 7 wherein the reaction further comprises a solvent which is N,N-dimethylformamide (DMF), a halogenated solvent, tetrahydrofuran (THF), dimethylsulfoxide (DMSO), an alcohol, benzene, toluene, MeCN, or DME.
10. The process according to claim 7 wherein the aldehyde R₁CHO is a pyrimidine aldehyde of the formula:

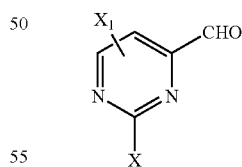

wherein X is YRₐ, and X₁ is hydrogen, or is defined as the optional substituent group on the R₁ moiety in Formula (I) to yield a compound of Formula (I) or a pharmaceutically acceptable salt thereof.

11. The process according to claim 1 wherein the compound of Formula (I) is:
  1-(1,3-Dihydroxyprop-2-yl)-4-(4-fluorophenyl)-5-[2-(4-fluorophenoxy)pyrimidin-4-yl]imidazole;
  1-(1,3-Dihydroxyprop-2-yl)-4-(4-fluorophenyl)-5-(2-phenoxypyrimidin-4-yl)imidazole;

1-(1-Hydroxy-2-phenyleth-2-yl)-4-(4-fluorophenyl)-5-(2-phenoxypyrimidin-4-yl)imidazole; or 1-(1,3-Dihydroxyprop-2-yl)-4-(4-fluorophenyl)-5-[2-(4-methylphenoxy)pyrimidin-4-yl]imidazole;

or a pharmaceutically acceptable salt thereof.

12. The process according to claim 1 wherein $R_1$ is a 4-pyrimidinyl ring substituted in the 2-position.

13. The process according to claim 12 wherein the $R_a$ moiety is an optionally substituted aryl or arylalkyl.

14. The process according to claim 1 wherein the $R_a$ moiety is substituted one or more times with halogen; $C_{1-4}$ alkyl; halosubstituted alkyl; hydroxy; hydroxy substituted $C_{1-4}$ alkyl; $(CR_{10}R_{20})q$ $C_{1-4}$ alkoxy; $(CR_{10}R_{20})qS(O)_m$alkyl; $(CR_{10}R_{20})qS(O)_m$ aryl; $(CR_{10}R_{20})qC(O)OR_{11}$; $(CR_{10}R_{20})qC(O)R_{11}$; $(CR_{10}R_{20})qOC(O)R_c$; —O—(CH$_2$)s-O—; $(CR_{10}R_{20})qNR_{13}R_{14}$; $(CR_{10}R_{20})qN(R_{10})C(O)R_b$; $(CR_{10}R_{20})qC(O)NR_{13}R_{14}$; $(CR_{10}R_{20})qC(O)NR_{10}R_c$; $(CR_{10}R_{20})qS(O)_2NR_{13}R_{14}$; $(CR_{10}R_{20})qS(O)_2$ $NR_{10}R_c$; $(CR_{10}R_{20})qN(R_{10})S(O)_2$ $R_c$; cyano, nitro, N-heterocyclyl ring which ring has from 5 to 7 members and optionally contains an additional heteroatom selected from oxygen, sulfur or $NR_{15}$; aryl; arylalkyl; aryloxy; or arylalkyloxy; and wherein the aryl, arylalkyl, aryloxy and arylalkyloxy may be optionally substituted themselves one to two times by halogen; hydroxy; hydroxy substituted alkyl; $C_{1-10}$ alkoxy; $S(O)_m$ alkyl; amino, $NR_7R_{17}$ group; $C_{1-4}$ alkyl, or halosubstituted $C_{1-4}$alkyl;

q is 0 or an integer having a value of 1 to 4; and $R_c$ is $C_{1-6}$ alkyl, $C_{3-7}$ cycloalkyl, aryl, aryl $C_{1-4}$ alkyl, heteroaryl, heteroaryl $C_{1-4}$alkyl, heterocyclyl, or a heterocyclyl $C_{1-4}$ alkyl moiety, wherein all of these moieties may be optionally substituted.

15. The process according to claim 1 wherein the $R_a$ is phenyl and the substituent group is halogen, halosubstituted alkyl, hydroxy, cyano, alkyl, aryl, alkoxy, aryloxy, arylalkyloxy, alkylthio, alkylsulfonyl, aminocarbonyl, acetamido, propionamido or methylenedioxy, or $R_a$ is tetrazole, or methyltetrazolyl.

16. The process according to claim 13 wherein $R_4$ is an optionally substituted phenyl.

17. The process according to claim 16 wherein the phenyl is substituted one or more times independently by halogen, $SR_5$, $S(O)R_5$, $OR_{12}$, halo-substituted-$C_{1-4}$ alkyl, or $C_{1-4}$ alkyl.

18. The process according to claim 1 wherein A is an optionally substituted aryl, heteroaryl or heterocyclic ring.

19. The process according to claim 18 wherein the aryl, heteroaryl or heterocyclic ring is optionally substituted independently one to three times by $C_{1-10}$ alkyl; halogen; halo substituted $C_{1-10}$ alkyl; $(CR_{10}R_{20})_tOR_{11}$; $(CR_{10}R_{20})_tNR_{13}R_{14}$; $(CR_{10}R_{20})_tS(O)_mR_{18}$, wherein m is 0, 1 or 2; SH; $NR_{10}C(Z)R_3$; or $NR_{10}S(O)_mR_8$; and t is 0, or an integer of 1 to 4.

20. The process according to claim 1 wherein A is a substituted $C_{1-10}$ alkyl.

21. The process according to claim 20 wherein A is a $C_{1-10}$ alkyl substituted independently 1 to 3 times by halogen; halosubstituted $C_{1-10}$ alkyl; $C_{3-7}$cycloalkyl; $C_{1-10}$ alkoxy; hydroxy substituted $C_{1-10}$ alkoxy; halosubstituted $C_{1-10}$ alkoxy; $OR_{11}$; $S(O)mR_{18}$ (wherein m is 0, 1 or 2); $NR_{13}R_{14}$; $C(Z)NR_{13}R_{14}$; $S(O)_mNR_{13}R_{14}$; $NHS(O)_2R_{18}$; $C(Z)R_{11}$; $OC(Z)R_{11}$; $C(Z)OR_{11}$; $C(Z)NR_{11}OR_9$; $N(OR_6)C(Z)NR_{13}R_{14}$; $N(OR_6)C(Z)R_{11}$; $C(=NOR_6)R_{11}$; or $OC(Z)NR_{13}R_{14}$.

22. The process according to claim 21 wherein A is a hydroxy substituted $C_{1-10}$ alkyl.

23. The process according to claim 22 wherein $R_{22}$ is a hydroxy substituted $C_{1-10}$ alkyl.

24. The process according to claim 1 wherein $R_{22}$ is substituted independently, one or more times, by halogen; halosubstituted $C_{1-10}$ alkyl; $C_{1-10}$ alkoxy; hydroxy substituted $C_{1-10}$alkoxy; halosubstituted $C_{1-10}$ alkoxy; $OR_{11}$; $S(O)_m$ $R_{18}$; $NR_{13}R_{14}$; $C(Z)NR_{13}R_{14}$; $S(O)_mNR_{13}R_{14}$; $NHS(O)_2$ $R_{18}$; $C(Z)R_{11}$; $OC(Z)R_{11}$; $C(Z)OR_{11}$; $C(Z)NR_{11}OR_9$; $N(OR_6)C(Z)NR_{13}R_{14}$; $N(OR_6)C(Z)R_{11}$; $C(=NOR_6)R_{11}$; $OC(Z)NR_{13}R_{14}$; optionally substituted $C_{3-7}$ cycloalkyl; optionally substituted aryl; optionally substituted heteroaryl; or an optionally substituted heterocyclic moiety.

25. The process according to claim 24 wherein $R_{22}$ is substituted with $OR_{11}$; $S(O)mR_{18}$.

26. The process according to claim 25 wherein $R_{22}$ is substituted with $OR_{11}$ and $R_{11}$ is hydrogen, aryl or arylalkyl.

27. The process according to claim 24 wherein $R_{22}$ is a $C_{1-3}$ alkylene moiety.

28. The process according to claim 25 wherein A is an $C_{1-10}$ alkyl substituted by $OR_{11}$.

29. The process according to claim 26 wherein $R_{11}$ is hydrogen, and $R_{22}$ is a $C_{1-3}$ alkylene moiety.

30. The process according to claim 17 wherein the phenyl is substituted in the 4-position.

31. The process according to claim 30 wherein the 4-position is substituted by halogen.

32. The process according to claim 31 wherein the halogen is fluorine.

33. The process according to claim 1 wherein $R_1$ is 2-phenoxy-4-pyrimidinyl; $R_4$ is phenyl or phenyl substituted one or two times by fluoro, chloro, $C_{1-4}$ alkoxy, $S(O)_m$ alkyl, methanesulfonamido or acetamido; and $R_2$ is 1,3-dihydroxyprop-2-yl, or 1-hydroxy-2-phenylethy-2-yl.

34. The process according to claim 11 wherein the compound is 1-(1,3-Dihydroxyprop-2-yl)-4-(4-fluorophenyl)-5-(2-phenoxypyrimidin-4-yl)imidazole, or a pharmaceutically acceptable salt thereof.

35. A compound of the Formula (III)

wherein $R_1$ is a pyrimidinyl ring, which ring is substituted with Y—$R_a$ and optionally with an additional independent substituent selected from $C_{1-4}$ alkyl, halogen, hydroxyl, $C_{1-4}$ alkoxy, $C_{1-4}$ alkylthio, $C_{1-4}$ alkylsulfinyl, $CH_2OR_{12}$, amino, mono and di-$C_{1-6}$ alkyl substituted amino, an N-heterocyclyl ring which ring has from 5 to 7 members and optionally contains an additional heteroatom selected from oxygen, sulfur or $NR_{15}$, $N(R_{10})C(O)R_b$ or $NHR_a$;

$R_2$ is —C(H)(A)($R_{22}$);

A is an optionally substituted aryl, heterocyclyl, or heteroaryl ring, or A is a substituted $C_{1-10}$ alkyl;

Y is oxygen or sulfur;

Z is oxygen or sulfur;

$R_a$ is aryl, aryl$C_{1-6}$alkyl, heterocyclic, heterocyclyl$C_{1-6}$ alkyl, heteroaryl, heteroaryl$C_{1-6}$alkyl, wherein each of these moieties may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl $C_{1-4}$alkyl, heterocyclyl, or heterocyclyl$C_{1-4}$ alkyl, wherein each of these moieties may be optionally substituted;

$R_{10}$ and $R_{20}$ is each independently selected from hydrogen or $C_{1-4}$ alkyl;

$R_{12}$ is hydrogen or $R_6$;

$R_{15}$ is $R_{10}$ or C(Z)-$C_{1-4}$ alkyl;

$R_{16}$ is $C_{1-4}$ alkyl, halo-substituted-$C_{1-4}$ alkyl, or $C_{3-7}$ cycloalkyl;

$R_{22}$ is a substituted $C_{1-10}$ alkyl.

36. The compound according to claim 35 wherein $R_1$ is a 4-pyrimidinyl ring substituted in the 2-position.

37. The compound according to claim 35 wherein the $R_a$ moiety is an optionally substituted aryl or arylalkyl.

38. The compound according to claim 37 wherein the $R_a$ moiety is substituted one or more times with halogen; $C_{1-4}$ alkyl; halosubstituted alkyl; hydroxy; hydroxy substituted $C_{1-4}$ alkyl; $(CR_{10}R_{20})q$ $C_{1-4}$ alkoxy; $(CR_{10}R_{20})qS(O)_m$alkyl; $(CR_{10}R_{10})qS(O)_m$ aryl; $(CR_{10}R_{20})qC(O)OR_{11}$; $(CR_{10}R_{20})qC(O)R_{11}$; $(CR_{10}R_{20})qOC(O)R_c$; —O—$(CH_2)$s-O—; $(CR_{10}R_{20})qNR_{13}R_{14}$; $(CR_{10}R_{20})qN(R_{10})C(O)R_b$; $(CR_{10}R_{20})qC(O)NR_{13}R_{14}$; $(CR_{10}R_{20})qC(O)NR_{10}R_c$; $(CR_{10}R_{20})qS(O)_2NR_{13}R_{14}$; $(CR_{10}R_{20})qS(O)_2$ $NR_{10}R_c$; $(CR_{10}R_{20})qN(R_{10})S(O)_2$ $R_c$; cyano, nitro, N-heterocyclyl ring which has from 5 to 7 members and optionally contains an additional heteroatom selected from oxygen, sulfur or $NR_{15}$; aryl; arylalkyl; aryloxy; or arylalkyloxy; and wherein the aryl, arylalkyl, aryloxy and arylalkyloxy may be optionally substituted themselves one to two times by halogen; hydroxy; hydroxy substituted alkyl; $C_{1-10}$ alkoxy; $S(O)_m$ alkyl; amino, $NR_7R_{17}$ group; $C_{1-4}$ alkyl, or halosubstituted $C_{1-4}$alkyl;

q is 0 or an integer having a value of 1 to 4; and $R_c$ is $C_{1-6}$ alkyl, $C_{3-7}$ cycloalkyl, aryl, aryl $C_{1-4}$ alkyl, heteroaryl, heteroaryl $C_{1-4}$alkyl, heterocyclyl, or a heterocyclyl $C_{1-4}$ alkyl moiety, wherein all of these moieties may be optionally substituted.

39. The compound according to claim 35 wherein the $R_a$ is phenyl and the substituent group is halogen, halosubstituted alkyl, hydroxy, cyano, alkyl, aryl, alkoxy, aryloxy, arylalkyloxy, alkylthio, alkylsulfonyl, aminocarbonyl, acetamido, propionamido or methylenedioxy, or Ra is tetrazole, or methyltetrazolyl.

40. The compound according to claim 35 wherein A is an optionally substituted aryl, heteroaryl or heterocyclic ring.

41. The compound according to claim 40 wherein the aryl, heteroaryl or heterocyclic ring is optionally substituted independently one to three times by $C_{1-10}$ alkyl; halogen; halo substituted $C_{1-10}$ alkyl; $(CR_{10}R_{20})_tOR_{11}$; $(CR_{10}R_{20})_t$ $NR_{13}R_{14}$; $(CR_{10}R_{20})_tS(O)_mR_{18}$, wherein m is 0, 1 or 2; SH; $NR_{10}C(Z)R_3$; or $NR_{10}S(O)_mR_8$; and t is 0, or an integer of 1 to 4.

42. The compound according to claim 35 wherein A is a substituted $C_{1-10}$ alkyl.

43. The compound according to claim 42 wherein A is a $C_{1-10}$ alkyl substituted independently 1 to 3 times by halogen; halosubstituted $C_{1-10}$ alkyl; $C_{3-7}$cycloalkyl; $C_{1-10}$ alkoxy; hydroxy substituted $C_{1-10}$ alkoxy; halosubstituted $C_{1-10}$alkoxy; $OR_{11}$; $S(O)mR_{18}$ (wherein m is 0, 1 or 2); $NR_{13}R_{14}$; $C(Z)NR_{13}R_{14}$; $S(O)_mNR_{13}R_{14}$; $NHS(O)_2R_{18}$; $C(Z)R_{11}$; $OC(Z)R_{11}$; $C(Z)OR_{11}$; $C(Z)NR_{11}OR_9$; $N(OR_6)C(Z)NR_{13}R_{14}$; $N(OR_6)C(Z)R_{11}$; $C(=NOR_6)R_{11}$; or $OC(Z)NR_{13}R_{14}$.

44. The compound according to claim 43 wherein A is a hydroxy substituted $C_{1-10}$ alkyl.

45. The compound according to claim 44 wherein $R_{22}$ is a hydroxy substituted $C_{1-10}$ alkyl.

46. The compound according to claim 35 wherein $R_{22}$ is substituted independently, one or more times, by halogen; halosubstituted $C_{1-10}$ alkyl; $C_{1-10}$ alkoxy; hydroxy substituted $C_{1-10}$ alkoxy; halosubstituted $C_{1-10}$ alkoxy; $OR_{11}$; $S(O)_m$ $R_{18}$; $NR_{13}R_{14}$; $C(Z)NR_{13}R_{14}$; $S(O)_mNR_{13}R_{14}$; NHS$(O)_2$ $R_{18}$; $C(Z)R_{11}$; $OC(Z)R_{11}$; $C(Z)OR_{11}$; $C(Z)NR_{11}OR_9$; $N(OR_6)C(Z)NR_{13}R_{14}$; $N(OR_6)C(Z)R_{11}$; $C(=NOR_6)R_{11}$; $OC(Z)NR_{13}R_{14}$; optionally substituted $C_{3-7}$ cycloalkyl; optionally substituted aryl; optionally substituted heteroaryl; or an optionally substituted heterocyclic moiety.

47. The compound according to claim 46 wherein $R_{22}$ is substituted with $OR_{11}$; $S(O)mR_{18}$.

48. The compound according to claim 47 wherein $R_{22}$ is substituted with $OR_{11}$ and $R_{11}$ is hydrogen, aryl or arylalkyl.

49. The compound according to claim 48 wherein $R_{22}$ is a $C_{1-3}$ alkylene moiety.

50. The compound according to claim 49 wherein A is an $C_{1-10}$ alkyl substituted by $OR_{11}$.

51. The compound according to claim 48 wherein $R_{11}$ is hydrogen, and $R_{22}$ is a $C_{1-3}$ alkylene moiety.

* * * * *